(12) United States Patent
Burdea et al.

(10) Patent No.: US 10,694,990 B2
(45) Date of Patent: Jun. 30, 2020

(54) BIMANUAL COMPUTER GAMES SYSTEM FOR DEMENTIA SCREENING

(71) Applicant: Bright Cloud International Corporation, Highland Park, NJ (US)

(72) Inventors: Grigore C. Burdea, Highland Park, NJ (US); Gregory P. House, Doylestown, PA (US)

(73) Assignee: Bright Cloud International Corporation, Highland Park, NJ (US)

( * ) Notice: Subject to any disclaimer, the term of this patent is extended or adjusted under 35 U.S.C. 154(b) by 678 days.

(21) Appl. No.: 14/841,042

(22) Filed: Aug. 31, 2015

(65) Prior Publication Data

US 2016/0038075 A1     Feb. 11, 2016

Related U.S. Application Data

(63) Continuation-in-part of application No. 14/032,360, filed on Sep. 20, 2013, now Pat. No. 9,724,598.

(Continued)

(51) Int. Cl.
  *A63F 13/218*   (2014.01)
  *A61B 5/00*   (2006.01)
  (Continued)

(52) U.S. Cl.
  CPC .......... *A61B 5/4088* (2013.01); *A63F 13/06* (2013.01); *A63F 13/211* (2014.09); *A63F 13/44* (2014.09);
  (Continued)

(58) Field of Classification Search
  CPC ............. G06F 19/3481; A63F 13/2218; A61B 5/1124; A61B 5/1125; A61B 5/02444
  (Continued)

(56) References Cited

U.S. PATENT DOCUMENTS

| 63,334,778 | 1/2002 | Brown |
| 2007/0136093 A1* | 6/2007 | Rankin ............... G06F 19/3431 705/2 |

(Continued)

OTHER PUBLICATIONS

Cameirão et al. "Neurorehabilitation using the virtual reality based Rehabilitation Gaming System: methodology, design, psychometrics, usability and validation" 2010.*
(Continued)

*Primary Examiner* — Omkar A Deodhar
*Assistant Examiner* — Ross A Williams
(74) *Attorney, Agent, or Firm* — McCarter & English, LLP

(57) ABSTRACT

The majority of cognitive virtual reality (VR) applications have been for therapy, and not cognitive screening/scoring. Provided herein is the BrightScreener™ and its first pilot feasibility study for evaluating elderly with various degrees of cognitive impairment. BrightScreener is a portable (laptop-based) serious-gaming system which incorporates a bimanual game interface for more ecological 3D interaction with virtual worlds. A pilot study determined that Bright-Screener is able to differentiate levels of cognitive impairment based solely on game performance, as well as to evaluate the technology acceptance by the target population. Subsequent group analysis of the Pearson correlation coefficient showed a high degree of correlation between the subjects' MMSE scores and their Composite Game Scores (0.90, |P|<0.01). Despite the small sample size (n=11), results suggest that serious-gaming strategies can be used as a digital technique to stratify levels of Cognitive Impairment. This may be an alternative to conventional standardized scoring for Mild Cognitive Impairment and Dementia, especially for patients with hearing and speech deficits.

17 Claims, 22 Drawing Sheets

Related U.S. Application Data

(60) Provisional application No. 62/043,810, filed on Aug. 29, 2014, provisional application No. 61/869,857, filed on Aug. 26, 2013, provisional application No. 61/704,165, filed on Sep. 21, 2012.

(51) Int. Cl.
| | |
|---|---|
| *G09B 5/00* | (2006.01) |
| *A63F 13/44* | (2014.01) |
| *A63F 13/67* | (2014.01) |
| *G06F 19/00* | (2018.01) |
| *A63F 13/20* | (2014.01) |
| *A63F 13/211* | (2014.01) |

(52) U.S. Cl.
CPC .......... *A63F 13/67* (2014.09); *G06F 19/3481* (2013.01); *G09B 5/00* (2013.01)

(58) Field of Classification Search
USPC ............... 463/1–6, 35, 37, 40–42; 482/4
See application file for complete search history.

(56) References Cited

U.S. PATENT DOCUMENTS

| | | | |
|---|---|---|---|
| 2012/0108909 A1* | 5/2012 | Slobounov | A61B 5/1124 600/300 |
| 2012/0157263 A1 | 6/2012 | Sivak | |

OTHER PUBLICATIONS

Wu, CY. et al., "Randomized trial of distributed constraint-induced therapy versus bilateral arm training for the rehabilitation of upper-limb motor control and function after stroke." Neurorehabil Neural Repair. 2011, vol. 25(2), pp. 130-139.

Burdea, GC. "Virtual rehabilitation—benefits and challenges." Methods Inf Med. 2003; vol. 42(5), pp. 519-523.

Brooks, CA. et al., "Traumatic brain injury: designing and implementing a population-based follow-up system." Arch Phys Med. Rehabil. 1997; vol. 78(8), pp. 26-30.

Lin, KC. et al., "The effects of bilateral arm training on motor control and functional performance in chronic stroke: a randomized controlled study." Neurorehabil Neural Repair. 2010; vol. 24(1), pp. 42-51.

Optale, G. et al., "Controlling memory impairment in elderly adults using virtual reality memory training: a randomized controlled pilot study." Neurorehabil Neural Repair. 2010; vol. 24(4), pp. 348-357.

Burdea, GC. et al., "The Rutgers Arm II rehabilitation system—a feasibility study." IEEE Trans Neural Sys Rehab Eng, vol. 18(5), pp. 505-514.

Burke, J.W., et al., "Optimising engagement for stroke rehabilitation using serious games", Vis. Comput, 2009, pp. 1085-1099, Springer Publishing.

Rabadi, MH, et al., "Intensive nutritional supplements can improve outcomes in stroke rehabilitation", Neurology, 2008, pp. 1856-1861. AAN Enterprises.

Roger, VL. et al., "Executive summary: heart disease and stroke statistics—2012 update: a report from the American Heart Association.", Circulation, 2012; vol. 125(1), pp. 188-197.

Cauraugh, JH. et al., "Bilateral movement training and stroke motor recovery progress: a structured review and meta-analysis." Hum. Mov. Sci., 2010; vol. 29(5), pp. 853-870.

Ausenda, CD. et al., "Transfer of motor skill learning from the healthy hand to the paretic hand in stroke patients: a randomized controlled trial." Eur. J. Rehabil Med., 2011; vol. 47(3), pp. 417-425.

Wang, M. et al., "Neuronal basis of age-related working memory decline." Nature, 2011; vol. 476(7359), pp. 210-213.

Duncan, PW. et al., "Reliability of the Fugl-Meyer assessment of sensorimotor recovery following cerebrovascular accident." Phys Ther. 1983; vol. 63(10), pp. 1606-1610.

Unity Technologies, Reference Manual. San Francisco, CA., 2010.

Sixense Entertainment, Razer Hydra Master Guide, pp. 1-11, 2011.

CNet Leap Motion controller review: Virtual reality for your hands. Jul. 22, 2013. http://www.cnet.com/products/leap-motion-controller/.

* cited by examiner

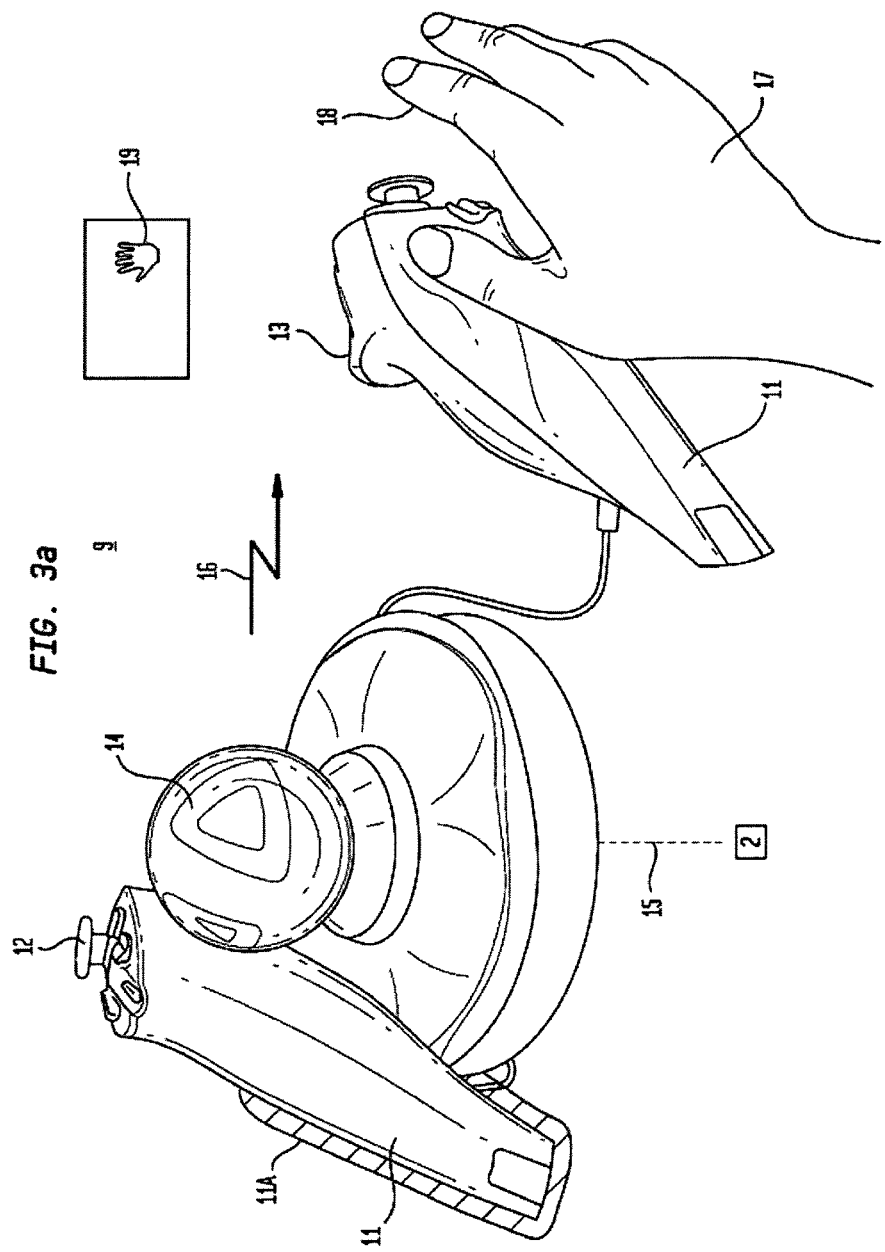

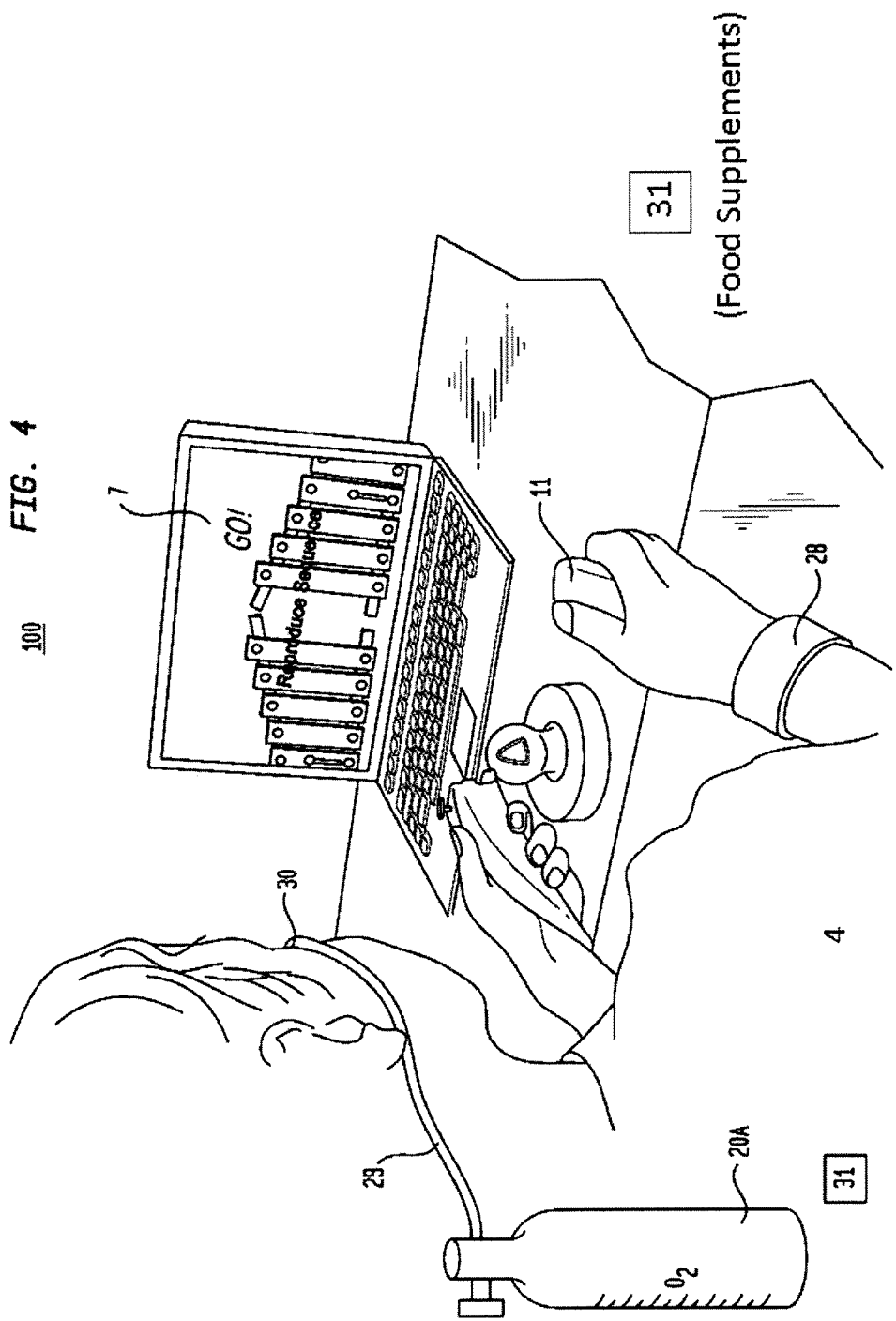

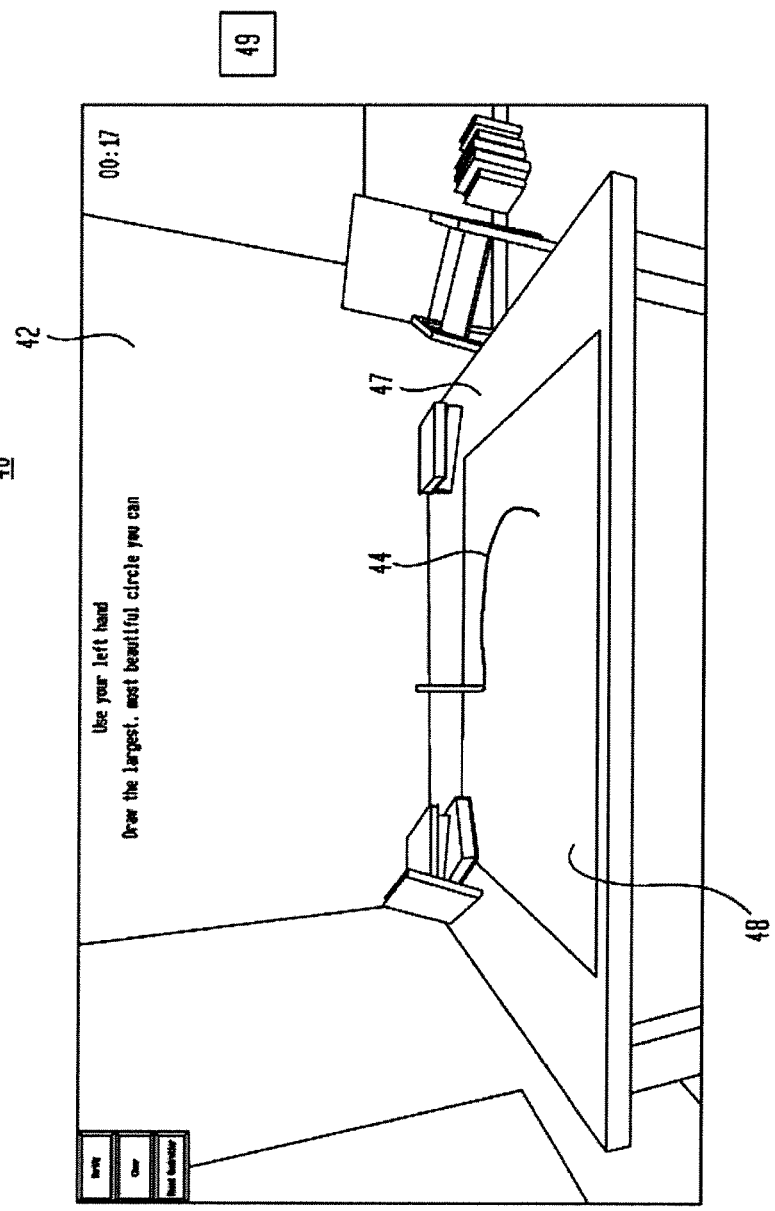

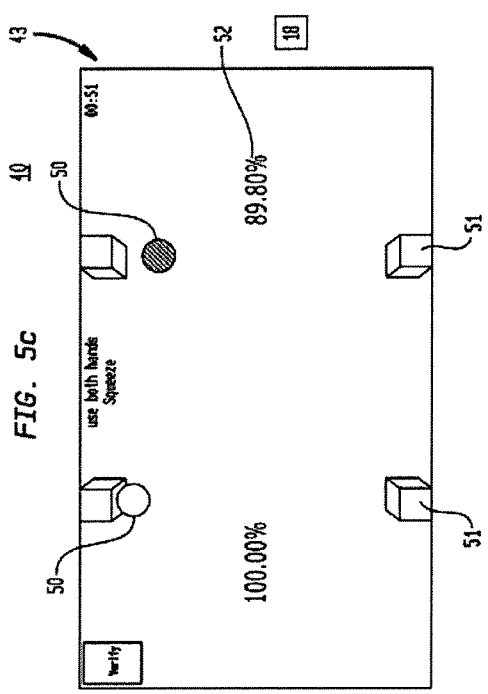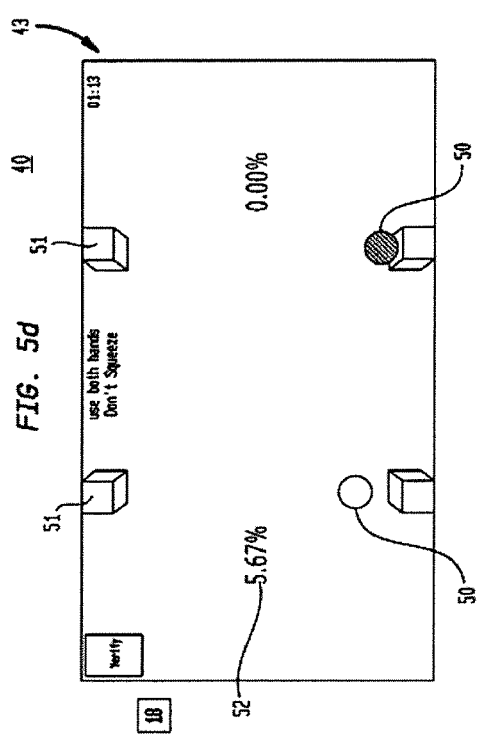

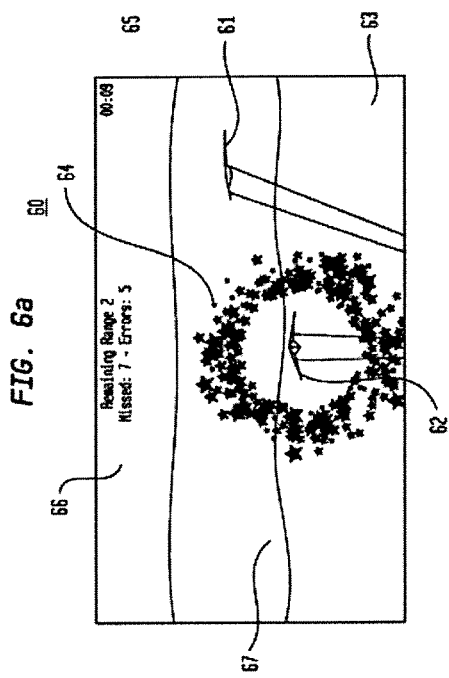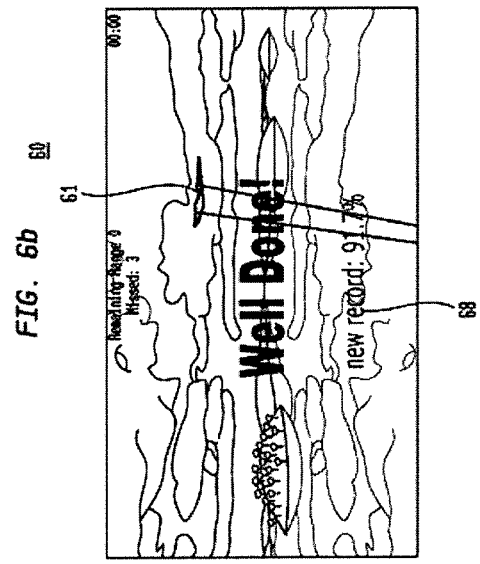

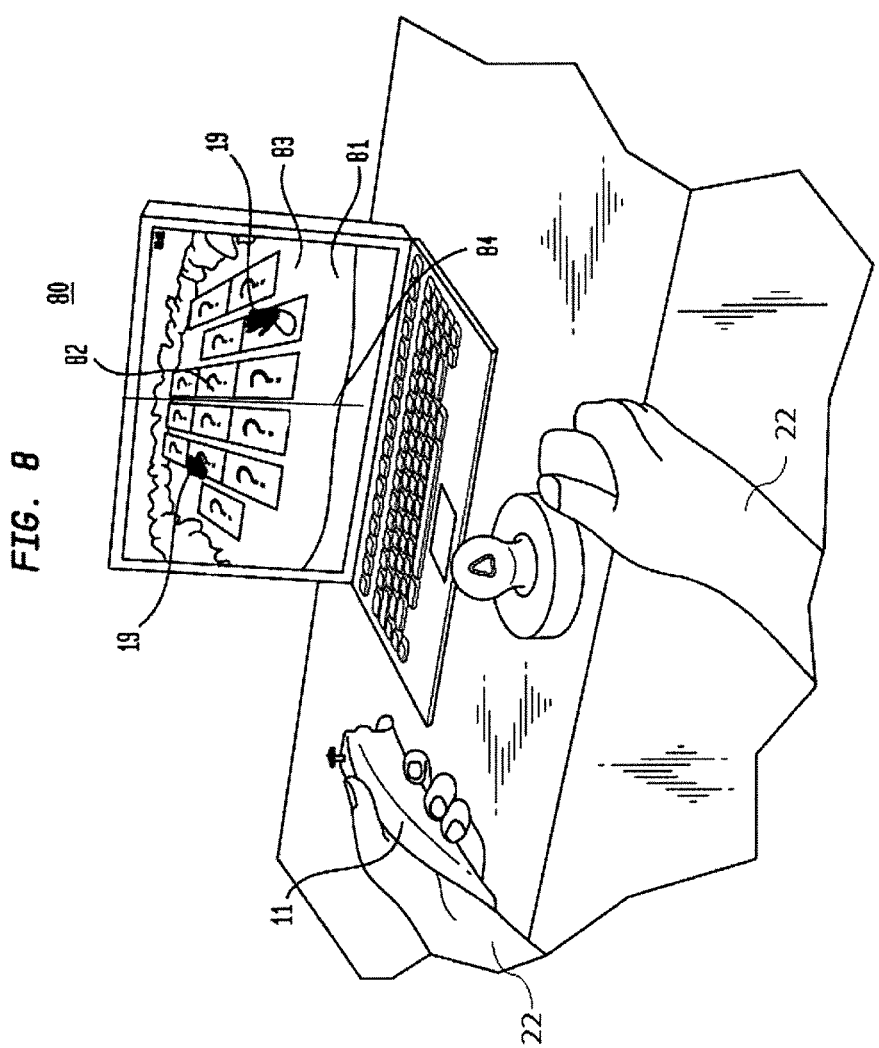

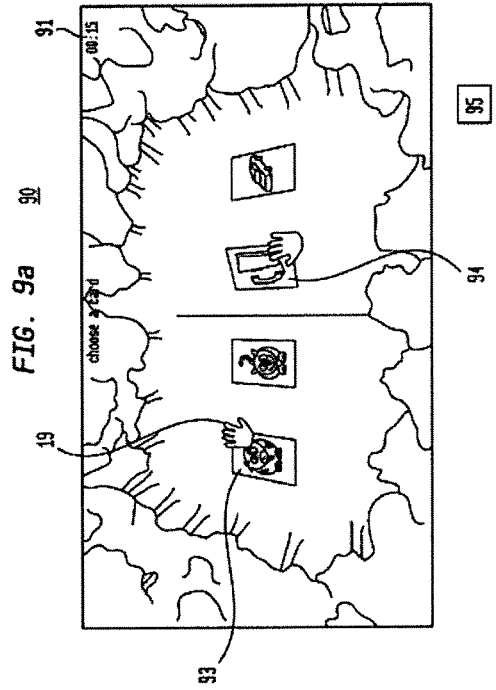
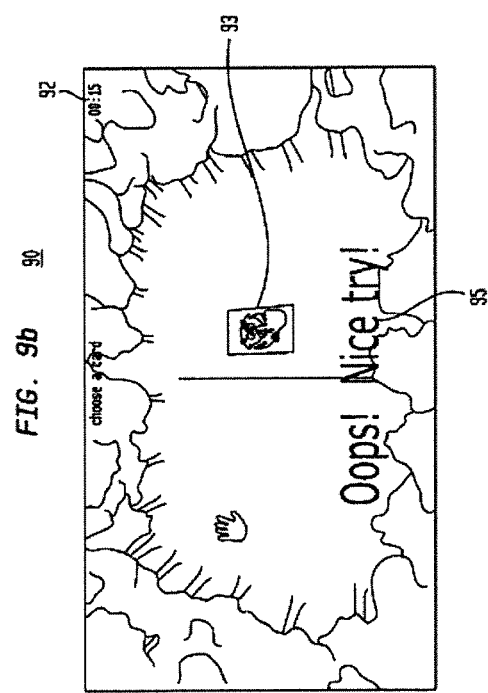

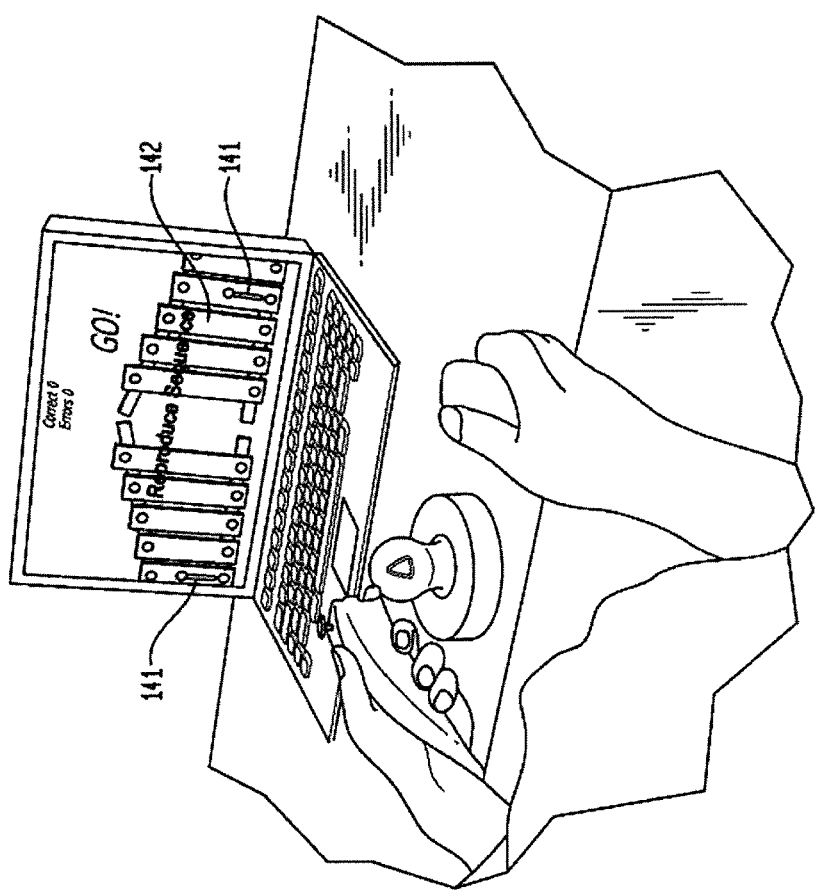

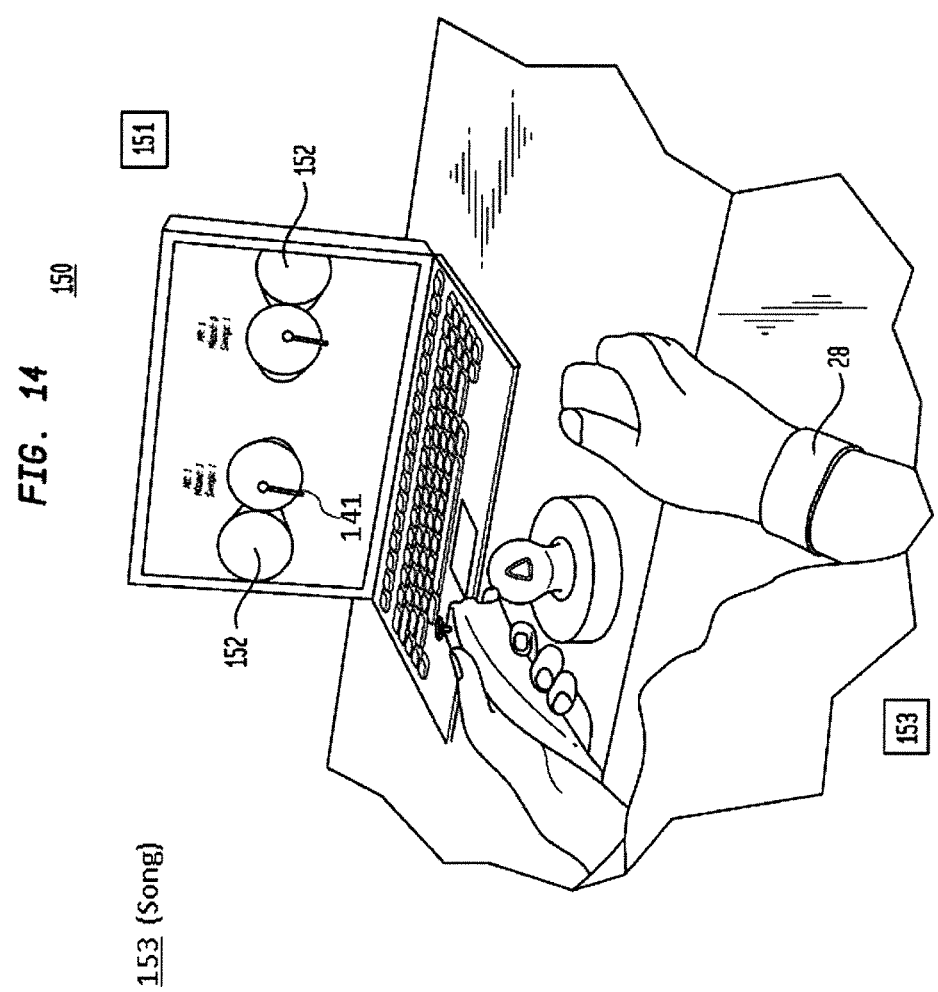

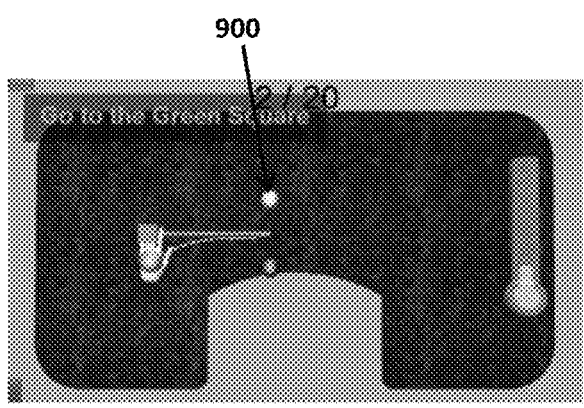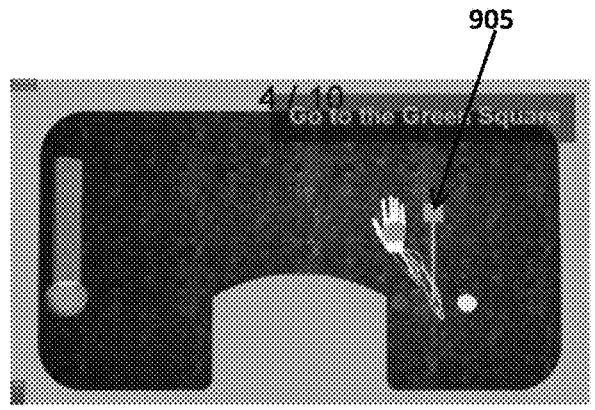
FIG. 17 A    FIG. 17 B

BIMANUAL COMPUTER GAMES SYSTEM FOR DEMENTIA SCREENING

CROSS REFERENCE TO RELATED APPLICATIONS

This application claims the benefit of and priority to U.S. Provisional Patent Application Ser. No. 62/043,810, filed Aug. 29, 2014. This application is also a Continuation-in-Part of, and claims the benefit of U.S. patent application Ser. No. 14/032,360, "Bimanual Integrative Virtual Rehabilitation Systems and Methods" filed on Sep. 20, 2013, which claims priority and benefit of U.S. Provisional Application Nos. 61/869,857, filed on Aug. 26, 2013 and 61/704,165, filed on Sep. 21, 2012. The entirety of all these applications is incorporated herein by reference.

BACKGROUND OF THE INVENTION

Stroke is the leading cause of disability in the US, with 795,000 Americans suffering one each year. See Reference No. 1. All references are listed at the end of the specification. Traditional physical rehabilitation of the paretic arm involves passive movement, compensatory training on the less involved arm, electrical stimulation, to which more recently has been added constraint induced therapy to combat learned non-use of the hemiplegic hand. See Reference No. 2. These are uni-manual training approaches involving a single arm which do not take into account the prevalence of activities of daily living (ADLs) which involve both arms.

Another drawback of uni-manual training is diminished neural cross talk to mirror motor areas associated with bimanual activities. A meta analysis of 48 stroke studies to determine the cumulative effect of bilateral arm training on motor capabilities post-stroke (Reference No. 3) did however find a significant effect post-training involving bimanual repeated reach movements timed to auditory cues. Another argument in favor of bilateral training is a recent randomized controlled study of stroke patients at the end of their outpatient therapy. See Reference No. 4. Researchers found, for the first time, that training the healthy arm (in a peg-board filling task) resulted in a 23% functional improvement in the non-trained paretic arm. Researchers also observed improvement in bilateral tasks performance in the experimental group. The control group, which did not train, had no significant difference from baseline. These studies point to the untapped advantages of bimanual training and the present application.

It is known in the art that numerous task-related repetitions are needed to produce neural rewiring in the brain. Repetitions, while necessary to induce recovery through brain plasticity, can lead to a lack of engagement (attendance to task) by the patient due to boredom. Second only to the amount of practice, feedback on performance is a key element in motor training and a way to engage the patient. Knowledge of performance feedback can be provided by the therapist (present next to the patient), or through graphics in a virtual rehabilitation setting (Reference No. 5), where the therapist, may be remote. Virtual rehabilitation benefits focus, motivation, and provides intensive training without boredom.

Stroke survivors, as well as other patient populations (such as those post traumatic brain injury—TBI) present with both motor and cognitive deficits. See Reference No. 6. Typically their short term and long term memory are affected, as are decision making (executive function), and the ability to focus. Most stroke patients also get depressed. Under the current fractionated care system, such patients are attended by therapists, as well as psychologists or psychiatrists, and speech language pathologists in separate sessions. This care delivery method is costly and does not exploit fully the mind-body continuum. As opposed to patients who are post-TBI and predominantly young, the elderly form the majority of stroke survivors. For them, the situation worsens due to age related cognitive decline. See Reference No. 7.

One age-related cognitive deficit is diminished ability for split attention (or dual-tasking). These patients need a system designed from the start for integrative cognitive and motor therapy, in order to minimize costs and maximize outcomes. Such system would use therapeutic games that pose both cognitive and whole arm motor demands, and train grasping in dual tasks. The system should automatically adapt to the patient's functioning level, thus making games winnable, so to improve morale (reduce depression). Games, such as cognitive games, mediate many repetitions, so to facilitate improvement or at least maintenance of cognitive function over time. Users that benefit most are the elderly with mild cognitive impairments, precursor to full-blown dementia.

There are indications that bimanual training induces higher functional improvements compared to uni-manual training. A recent randomized controlled study (Reference No. 8) was performed on patients chronic post-stroke, half doing bimanual training and the controls doing training of the affected arm, with some coping mechanism (assistance) from the other arm. While both groups had the same training duration and intensity, those doing bimanual training had a 9 points larger improvement in motor function (as measured by their Fugl-Meyer Assessment [reference 9] scores) vs. controls. More recently a randomized study of 36 nursing home residents was performed to try to lessen cognitive decline and improve memory function. See Reference 10. The experimental group showed significant improvements in long-term recall and in several other aspects of cognition, while controls showed progressive decline. The above findings motivate the system described here, a bimanual therapy system that simultaneously addresses motor and cognitive impairments of patients post-stroke, post TBI, or those with Mild Cognitive Impairments (MCI) developing into dementia. This novel integrative therapy uses custom, adaptable, bimanual virtual reality games, which combine into gradated therapy sessions.

With the aging of the population the number of elderly affected by Dementia (including Alzheimer's disease) has grown significantly. In standard of care a clinician (typically a neuropsychologist, registered nurse, clinical social worker, or other medical professional) administers a standardized test which scores the individual's cognitive abilities.

An example of such standardized test is the Mini Mental State Exam (MMSE) (Reference No. 24) which scores cognitive ability or impairments on a scale of 0 (severely impaired) to 30 (normal cognition). This is a paper and pencil method, in which the clinician asks questions and scores the answers. These answers may involve orientation (determining place and time), arithmetic (subtractions by 7), writing a sentence, drawing after a given image, etc. The current method has major flaws:

First, it is dependent on individual's hearing. Typically the elderly are prone to hearing loss, and if not checked it can lead to miss diagnosis just because the person cannot hear the examiner's questions. Many elderly are wrongly diagnosed with Alzheimer's disease just because they have no working hearing aids.

Second, it requires a specialist to administer, and according to the Alzheimer's Association (Reference No. 26), more than 5 Million Americans are suffering from the ravages of this irreversible neurodegenerative disorder. Therefore there are just not enough qualified people to test them. This shortage will only grow with the increase in the number of people that require examination.

Third, there is a level of variability in the administration of the test, which may affect the outcome. An automated screening/assessment method would be preferable, as test administration is more uniform.

Fourth, if the patient has speech impairments, such as for those afflicted by Primary Progressive Aphasia, a rare form of dementia affecting men in their 40s and 50s, that their verbal responses to test questions may be not understood or wrongly interpreted by the examiner.

There is a need for a computerized screening system that can perform examinations, and use methods where the elderly's hearing and speech are less critical to get a more accurate result. A number of computerized diagnostic and therapy systems exist, including the web-based Lumosity (Reference No. 22). The limitation with these systems is that they are mouse-based, and uni-manual. Mouse interaction limits arm movement to a 2D plane, and uni-manual tasks are necessarily less complex/ecological than bimanual interactions. Thus the full potential of an individual's cognitive capacity may not be evaluated by these simplistic game simulations.

SUMMARY OF THE INVENTION

In accordance with an aspect of the present invention, systems and methods of providing therapy to a patient having a first arm, a first hand, a second arm and a second hand, are provided. In accordance with an aspect of the method, the following steps are performed: a video game is executed on a computer and action from the video game is portrayed on a display, and through sound, the action being viewed and heard by the patient. Then, the patient holds a first component of a game controller in the first hand and manipulates a button/trigger on the first component of the game controller with the first hand and moves the first component of the game controller with the first hand and the first arm to control a first avatar in the video game. The patient also holds a second component of a game controller in the second hand and manipulates a button/trigger on the second component of the game controller with the second hand and moves the second component of the game controller with the second hand and the second arm to control a second avatar in the video game. The first component of the game controller is separate from the second component of the game controller and can be moved independently and in 3 dimensional space, from the second component of the game controller. The game controller sends one or more signals representative of a position of the button/trigger on the first component, of a position of the button on the second component, of a motion of the first component in 3D space and of a motion of the second component in 3D space are reported by the game controller to the computer in real time (tens of measurements every second). The computer analyzes the one or more signals and controls the video game to control avatars and perform actions portrayed on the display and heard on computer speakers or headphones.

In accordance with another aspect of the present invention, the video game causes a displayed object to include one of two codes wherein a first code indicates that the displayed object can be moved with the first component of the controller and a second code indicates that the displayed object can be moved with the second component of the controller. The two codes can be, for example, different object or avatar colors, where an avatar can only manipulate like-colored virtual objects.

In accordance with a further aspect of the invention, when the video game causes a displayed object to include one of two codes, the computer only allows the displayed object to be moved by either the first component or the second component of the controller in accordance with the two codes.

In accordance with another aspect of the invention, the computer monitors and stores a set of information from the first component and the second component of the controller, the set of information including: (1) activation of the button on the first component of the controller; (2) movement of the first component of the controller; (3) activation of the button on the second component of the controller; and (4) movement of the second component of the controller. The computer then controls the video game and resulting action on the display in accordance the set of information. The computer can also analyze the set of information to determine progress of the patient by assigning scores to each video game and by counting the number of arm movement and finger flexion repetitions performed by the first component and by the second component of the controller. The computer can also determine the therapy intensity by determining the number of movement repetitions per unit time (minute).

In accordance with yet another aspect of the invention, while holding the first and second components of the controller the patient wears wrist weights on one or both forearms. The wrist weights may be of the same weight, or they may have different weights. For example, the weight worn on the plegic arm of a stroke patient may be lighter than the weight worn on the healthy arm. The patient may also be provided with extra oxygen through a flexible tube to the nose, so to increase oxygenation to the brain. The patient may consume food supplements designed to increase cognitive activity immediately prior to using the first and second components of the controller during video game play.

In accordance with yet another aspect of the invention, the computer controls the action displayed such that the action caused by the first component of the controller is the same as the action caused by the second component of the controller, even when the arms move dissimilarly. The computer measures the reach of each arm and adjusts the mapping between physical (real) arm movement and that of the corresponding avatar, such that both avatars contribute equally to the game.

Systems that perform the methods described herein are also provided. For example, a system can also include a computer, a video game executing on the computer, a display portraying action from the video game on a display, the action being viewable and heard by the patient, a game controller having a first hand-held component with a button and a second hand-held component with a button, wherein the first component is separate from the second component and can be moved independently from the second component and in 3D. The game controller sends one or more signals representative of a position of the button/trigger on the first component, of a position of the button/trigger on the second component, of a motion of the first component and of a motion of the second component are reported by the game controller in real time to the computer. The computer analyzes the one or more signals and controls the video game to control action portrayed on the display such that the action caused by the first component of the controller is the same as the action caused by the second component of the controller.

The computer can also cause all other processes described herein.

The controller may be a Leap Motion controller, in which case the patient interacts with the computer through hand gestures.

It is specified that some or all of these therapeutic games may be played with wrist weights, so to increase the physical exercise component of the integrative therapy. The wrist weights are those known in the art and commercially available. It is believed that for elderly users smaller weight values (such as 0.5 lb, 1 lb and 2 lb) are appropriate for use with the system described in this application.

It is specified that for younger or older patients the wrist weights may have different values, with the healthy arm wearing a larger weight than the injured arm.

Alternatively, weights can be applied to a handheld controller that is manipulated by the patient.

In accordance with another aspect of the present invention, a system of screening a patient for cognitive impairment is provided. This system comprises a computer, a videogame executing on the computer, and a display portraying action from the videogame, the action being viewable by the patient. The system also comprises a game controller connected to the computer, the game controller having one or more hand-held components with a button or trigger. The hand-held components may be moved independently. The game controller may be adapted to send to the computer one or more signals representative of a position of the hand-held component and a position of the button or trigger on the hand held component. The game controller may be adapted to send the one or more signal as the patient changes the position of the hand-held component and the position of the button or trigger on the hand-held component in response to action in the video game. The computer may be adapted to quantify a measure of cognitive impairment based on the one or more signals received by the controller and by compounding performance in one or more games.

In other embodiments of the present invention, the computer may measure the amount of time it takes a patient to complete a task in the video game and uses the time to generate a testing score of cognitive impairment. In other embodiments, the computer measures the precision of movement of the controller during performance of a task on the video game and uses that quantified precision of movement to generate a testing score of cognitive function. In yet other embodiments, the computer may measure both the precisions of movement of the controller during performance of a task and the time it takes to complete the task, and uses the quantified precision and time to generate a testing score of cognitive impairment.

Other embodiments of the present invention may comprise the computer accounting for the uni-manual or bimanual interaction modality with one or more videogames and adjusts the testing score accordingly. The computer may also adjust the measure of cognitive impairment based on the difficulty of the task performed in the video game.

Alternative embodiments of the invention may employ a computer that quantifies cognitive impairment based on the patient's performance in two or more different types of games by computing an aggregate or compound score for the evaluation session. In various embodiments, the computer may quantify cognitive impairment of the patient into one of the following cognitive bands: normal; mild cognitive impairment; moderate cognitive impairment; severe cognitive impairment.

In accordance with another aspect of the present invention, a method of screening a patient for cognitive impairment is provided. This method may comprise executing a video game on a computer and portraying action from the videogame on a display, the action on the display being viewable by the patient. The patient may hold a game controller comprising one or more hand-held components having a button or trigger, wherein the hand-held components can be moved independently. The patient may perform an action in the video game by moving the relative position of the hand-held component and manipulating the button or trigger on the hand-held component. The computer may receive a signal from the controller representative of the position of the hand-held component and the manipulation of the button or trigger. The computer may calculate a degree of cognitive impairment by quantifying the movement of the hand-held component and quantifying manipulation of the button or trigger on the hand-held component as they map to avatars in the games.

In another embodiment, the method may further comprise the computer measuring the amount of time it takes a patient to complete a task in the videogame and using that time to generate a testing score of cognitive impairment. Other embodiments may comprise the computer measuring the precision of movement of the controller during performance of a task on the videogame and using that quantified precision of movement to generate a testing score of cognitive function. Yet other embodiments may comprise the computer both measuring the precision of movement of the controller during performance of a task and measuring the time it takes a patient to complete the task in the video game, and using the quantified precision and time to generate a testing score of cognitive impairment.

In other embodiments of the present invention, the method may further comprise the computer adjusting the measure of cognitive impairment based on the difficulty of the task performed in the video game, and averaging performance scoring over a multitude of games played at different difficulty levels in a given evaluation session. Yet further, the computer may quantify cognitive impairment based on the patient's performance in two or more different types of games.

In various embodiments, the computer may quantify cognitive impairment based on the patient's performance, said performance being measured after the patient had undergone a tutorial session such that learning artifacts are minimized. In one or more embodiments the computer may further comprise the step of quantifying cognitive impairment of the patient into one of the following cognitive bands: normal; mild cognitive impairment; moderate cognitive impairment; severe cognitive impairment.

One or more aspects of the present invention may comprise a controller with exactly two hand-held components with a button or trigger, wherein the hand-held components can be moved independently from one another in each hand of the patient.

DESCRIPTION OF THE DRAWINGS

FIG. 3a illustrates a Razer Hydra bimanual game interface.

FIG. 4 illustrates a patient playing a game while wearing wrist weights and having an oxygen tube to the nose.

FIG. 5b illustrates an arm horizontal movement baseline.

FIG. 5c illustrates a flexion baseline for left and right index fingers.

FIG. 5d illustrates an extension baseline for left and right index fingers.

FIG. 6a illustrates a Kites game to train focusing.

FIG. 6b illustrates a Kites game summative performance feedback.

FIG. 8 illustrates a Card Island game to train short term visual and auditory memory.

FIG. 9a illustrates a card game training long term visual and auditory memory (delayed recall), showing Phase 1 of the game asking the patient to choose one card and remember its image and corresponding sound for later.

FIG. 9b illustrates a situation where, after a number of other games are played, the patient needs to recall the card initially selected. The patient was unsuccessful in that task.

FIG. 13 illustrates a Xylophone bimanual game.

FIG. 14 illustrates a Musical Drums bimanual game.

FIG. 17a illustrates a BrightScreener game tracking movement of a patient with normal working memory according to one embodiment of the present invention.

FIG. 17b illustrates a BrightScreener game tracking movement of a patient with abnormal working memory due to Alzheimer's disease, according to one embodiment of the present invention.

DESCRIPTION

Figure 1:
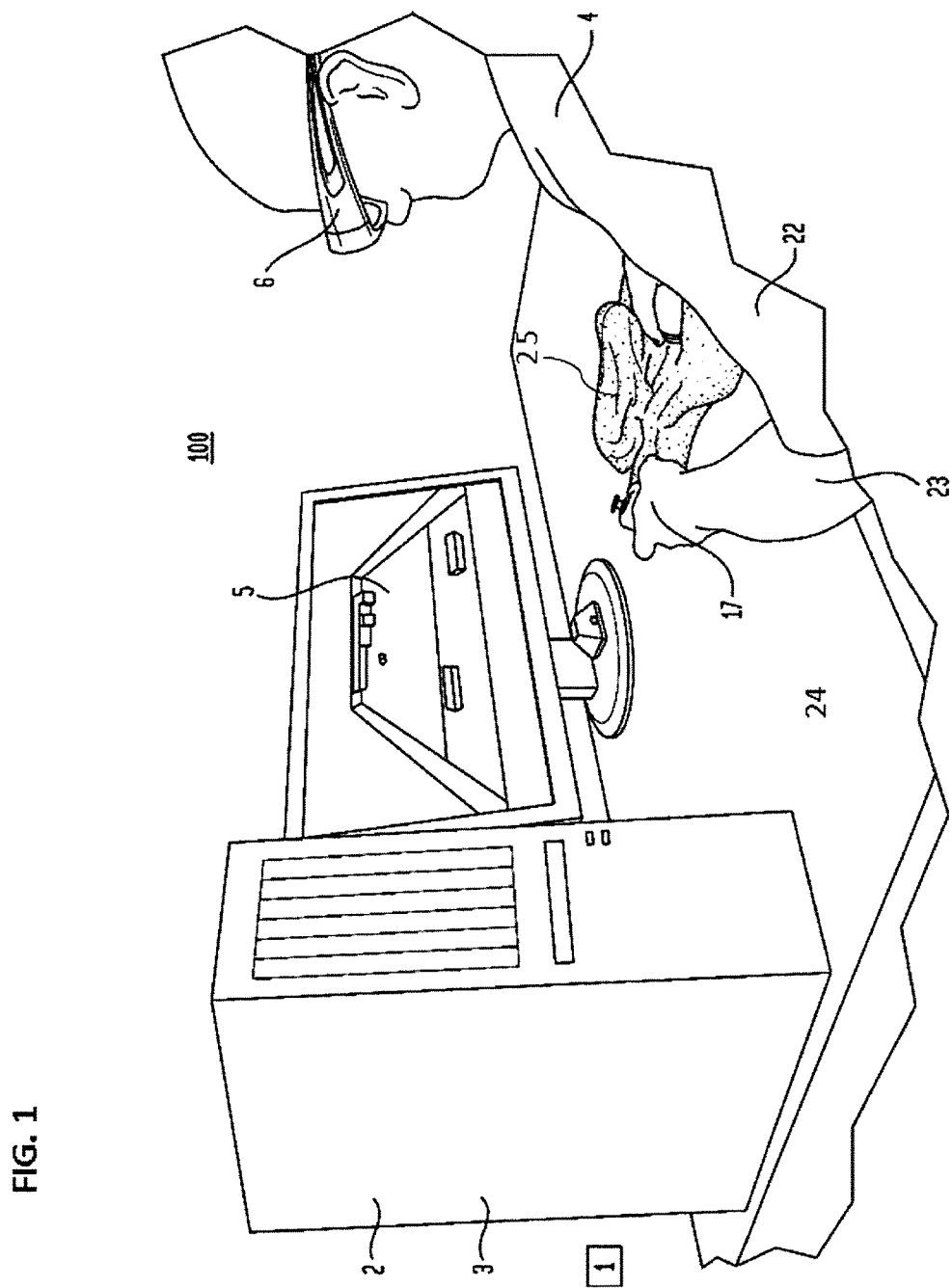
FIG. 1 illustrates a bimanual exercise system using a workstation, 3D (stereo) monitor, 3D glasses, a Hydra bimanual hand controller and a patient who rests the plegic arm on a towel so to minimize friction with the supporting table.

Referring to FIG. 1, the bimanual therapy system 100 consists of off-the shelf gaming hardware and a library of custom therapeutic games 1 written in Unity 3D Pro. See Reference 11. The games are rendered on a computer 2, such as those available in commerce. For example, the games 1 can be rendered by an HP Z600 graphics workstation with an nVidia "Quadro 2000" graphics accelerator 3, or subsequent models (FIG. 1). The graphics are in 3D, so to facilitate immersion and help the patient 4 in his manual tasks. Therefore the workstation 2 is connected to an Assus VG236H 3D monitor 5, and the patient 4 wears a pair of nVidia "3D Vision" active stereo glasses 6. A towel 25 is used to allow patient 4 to rest his arm 23 on table 24.

Figure 2:
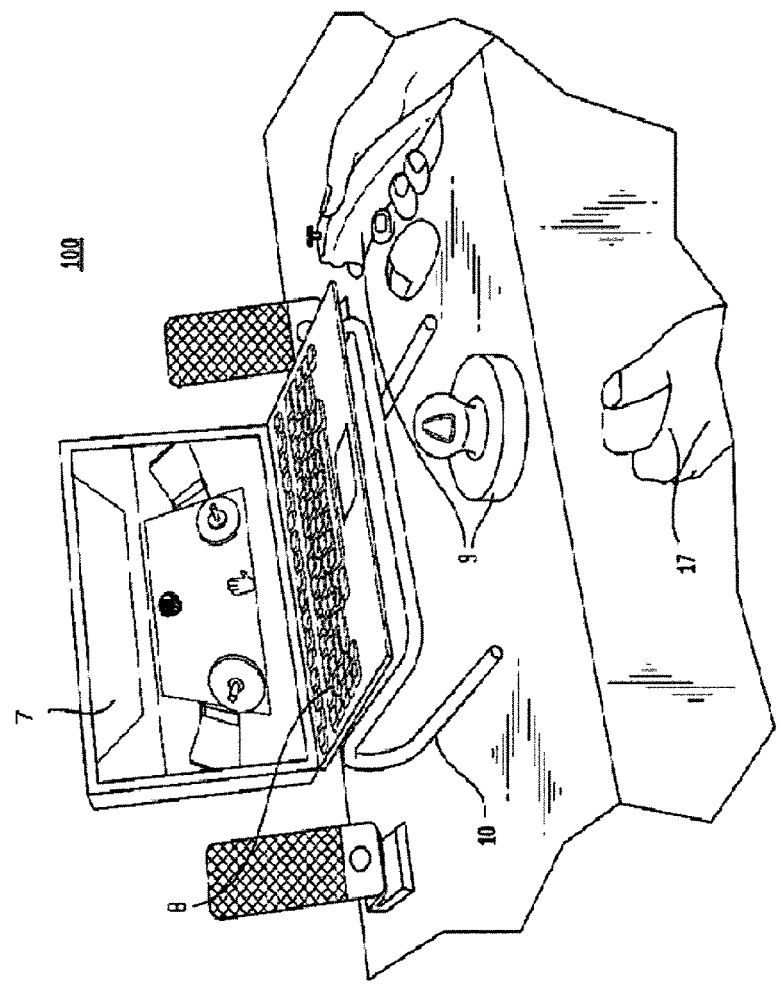
FIG. 2 illustrates a system using a gamer laptop placed on a cooling tray and the same Hydra bimanual hand controller.

Alternately the games 1 may be rendered on a 2D "gamer" laptop computer 7 such as the HP Envy with 17 inch diameter screen and nVidia GeForce GT 750M graphics accelerator 8 or subsequent models. The same bimanual game controller 9 may be used (FIG. 2), and the laptop 7 may be placed on a cooling tray 10, such as those available commercially. It is envisioned that other computers such as those "all-in-one" PCs available commercially, may be used as part of the bimanual integrative therapeutic system 100.

In one embodiment, the interaction with the games is mediated by a Razer Hydra bimanual interface (Reference 12) shown in FIG. 3a. It consists of two hand-held pendants 11, each with a number of buttons 12 and a trigger 13, and a stationary source 14 connected to the workstation 2 over an USB port 15. The source 14 generates the magnetic field 16 which allows the workstation 2 to track the 3D position and orientation of each hand 17 in real time. Of the many buttons on the pendants 11, the system 100 uses an analog trigger 13 so to detect the degree of flexion/extension of the patient's index fingers 18. The pressing of these analog triggers 13 controls the closing/opening of hand avatars 19, while the position/orientation of the hand avatars 19 is determined by the position/orientation of the corresponding Hydra pendants 11. The Hydra is calibrated at the start of each session by placing the two pendants 11 next to the source 14. Its work envelope is sufficient to detect hand 17 position for a patient 4 exercising in sitting.

Weights 11A can be provided which can be slipped over the pendant 11 to increase the difficulty for the patient. The weights can be provided in a variety of forms and they can be attached to the pendants 11 (both sides) by snaps, Velcro, and other mechanical attachments. Alternately, the weights 28 can be placed at the wrist.

Figure 3B:
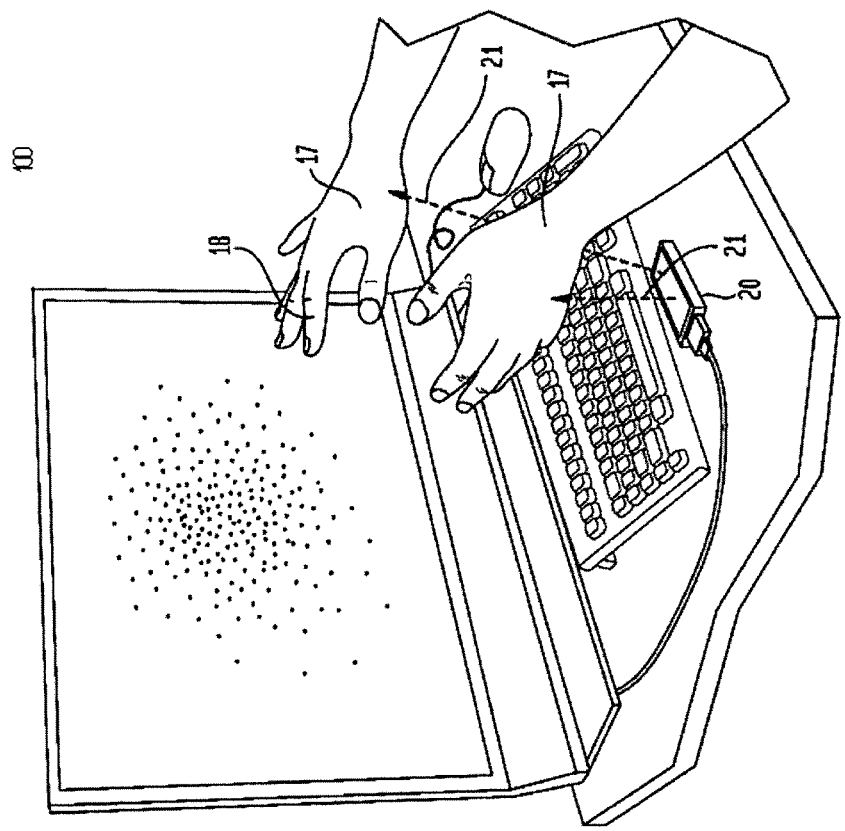
FIG. 3b illustrates a Leap Motion hand controller.

Alternately the system 100 can use a Leap Motion hand controller 20, as shown in FIG. 3b (see Reference 13). In this case the interaction is through hand 17 gestures, without the need for pendants 11. Detection of hand 17 and finger 18 movement is through infrared beams 21 emitted by the controller 20 and reflected off the hands 17 of the patient 4. It is appreciated that hands 17 need to be able to fully flex/extend fingers 18, so to assure proper measurement by the controller 20 through its infrared beams 21.

Figure 3C:
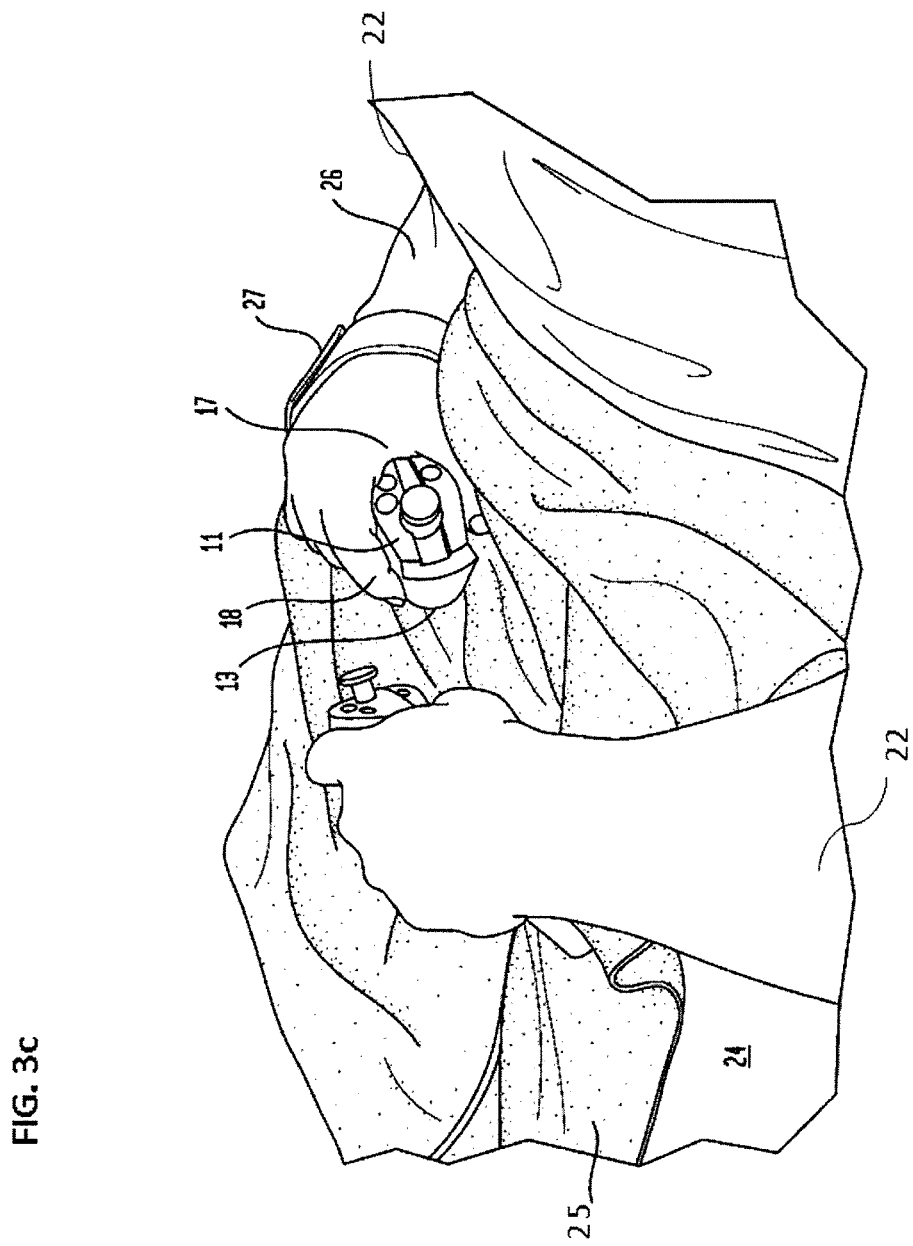
FIG. 3c illustrates a Velcro strip used to keep Hydra controller in the hand of a stroke patient with the forearm resting on a towel.

Stroke patients 4 in the acute stage (just after the neural infarct) have weak arms 22. Similarly, patients who are chronic post-stroke may have low gravity bearing capability. Some of them may also have spasticity (difficulty flexing/extending elbows 23 or fingers 18). Thus using the Hydra 9 with this population is different from use in normal play by healthy individuals. The adaptation in the present application is to place the weak arm 22 on a low-friction table 24, and use a small towel 25 under the forearm 26, so to minimize friction and facilitate forearm 26 movement (see FIG. 3c). Furthermore, for spastic patients who may have difficulty holding the Hydra pendant 11 in their spastic hand 17, the solution is to use Velcro strips 27 to position the index finger 18 properly over the analog trigger 13.

For stronger patients 4, or those without motor impairment to their arms 22 or hands 17, it is possible to play the games 1 while wearing wrist weights 28. The amount of added physical exertion is proportional to the size of weights 28, as well as the duration of the session played while wearing the wrist weights 28. It is appreciated that elderly users 4 will feel more comfortable while wearing smaller weights 28 (0.5 lb, 1 lb, 2 lb). FIG. 4 shows a patient 4 playing a game 1 using the Hydra pendants 11, while wearing wrist weights 28. It is envisioned that the size of the wrist weights 28 may be increased over the weeks of training, with larger weights worn in later weeks. It is also appreciated that the weights need not be the same for each arm, with the weaker arm having smaller weights.

It is further envisioned that while playing the cognitive games 1 on the system 100 which now has the commercial name of BrightBrainer™, the user 4 can also have an Oxygen tube 29 to the nose 30. The Oxygen tube 29 is of the type known in the art (transparent plastic), being small and flexible, and unencumbering to the user 4. Provision of extra Oxygen to the blood, brings extra oxygenation to the brain. This boosts the brain activity, as it facilitates energy generation and in turn helps neuronal activity. The oxygen is provided via a tank 30A.

In addition to (or instead of) wearing an Oxygen tube 29, the user 4 may choose to have food supplements 31 (such as dark chocolate, fatty fish, spinach, blueberries, walnuts, avocado, water intake increase). Such food supplements 31 need to be taken some time before the play on the system 100, so to be metabolized, and facilitate increased cognitive activity.

Therapeutic Games

Several games 1 were developed to be played either uni-manually or bimanually. This gives flexibility when the therapy focus is motor re-training (using uni-manual mode), or integrative cognitive retraining (using bimanual mode). The requirement for developing a multi-game 1 therapy system 100 stems from the need to address several cognitive areas (by targeted games 1), as well as to minimize boredom by alternating games 1 during a session.

In a sequence of sessions, the first sessions can be played uni-manually so users 4 learn the games 1. In the second part they progress to using both arms 22, and finally to wearing weights 28 for increased exercising demands and blood flow to the brain. It is also envisioned that in a sequence of sessions, the duration of play will be shorter in the first sessions, and progressively longer over the duration of therapy.

Baselines

Figure 5A:
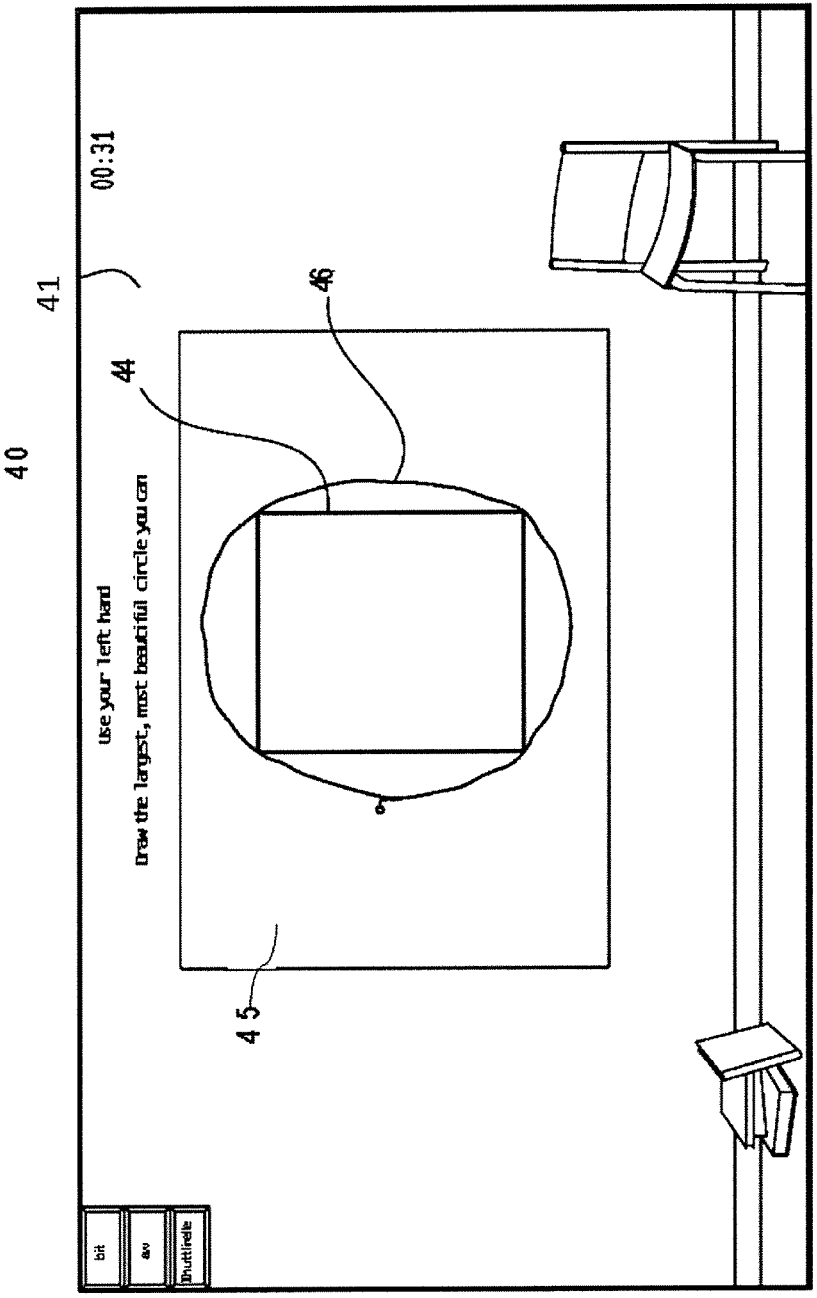
FIG. 5a illustrates an arm vertical movement baseline.

Each patient 4 is different, each day. It is therefore necessary to use baselines 40 to determine the patient's 4 motor capabilities, and adapt the games 1 accordingly. The system 100 uses three baselines, two for arm range 41, 42, and one for the index finger flexion/extension 43 using the analog trigger 13 on the Hydra pendant 11. As seen in FIG. 5a, the vertical baseline 41 asks the patient 4 to draw a circle 44 on a virtual blackboard 45. The software then fits a rectangle to the "circle" 44 and this range is used to map the arm 22 limited vertical range 46 to the full vertical space on the game 1 scene. The horizontal baseline 42 (FIG. 5b) is similar, except now the patient 4 is asked to draw a circle 44 on a virtual table 47 covered by a large sheet of paper 48.

During bimanual play sessions each arm 22 performs the baselines 42, and 42 in sequence, and each arm 22 has different gains 49 mapping real movement to avatar 19 movement in the virtual scene. Thus the movement of their respective hand avatars 19 appears equal (and normal) in the virtual world, something designed to motivate the patient 4. A further reason to present exaggerated movement of the paretic arm 22 when mapped to VR is the positive role image therapy has traditionally played. In other words, the patient 4 is looking at the display 5, not at the hand 17, and believes what he or she sees on the display. This technique is similar by that developed by Burdea et al. in U.S. application Ser. No. 12/422,254 "Method for treating and exercising patients having limited range of body motion," which is incorporated herein by reference. (See Reference 14).

The third baseline 43 measures the range of movement of the index 18 of each hand 17. Unlike the range baselines 41 and 42, done in sequence, the index baseline 43 is done simultaneously for both hands 17. As seen in FIG. 5c, the patient sees two spheres 50 that move vertically between target blocks 51, in proportion with the index 18 movement on each pendant trigger 13. First the patient 4 is instructed to flex, and the two balls 50 move up a certain percentage of full range. The baseline displays the finger-specific percentage 52 of full motion. Subsequently the patient 4 is asked to extend the index 18 of each hand 17 and the balls 50 move down, again a certain percentage of full range 52 (FIG. 5d). For spastic patients 4, the paretic index 18 will have little difficulty flexing, but substantial difficulty extending. The resulting limited range for the paretic index 18, and full range of the non-paretic one are then mapped to the hand avatars 19. The two hand avatars 19 will thus show full flexion and full extension during the games 1.

Games to Train Focusing

Two games were developed to train patient's 4 ability to focus. The Kites game 60 presents two kites 61, 62 flying over water 63, while the sound of wind is heard (FIG. 6a). One kite is green, one red, and they have to be piloted through like-colored target circles 64, 65. The circles 64,65 alternate randomly in their color and their position on the screen, and the difficulty of the game 60 is modulated by the speed of the circles 64, 65, the duration of the game 60, the visibility 66 (a foggy sky gives less time to react) and the presence of air turbulence (acting as a disturbance 67). The game 60 calculates the percentage 68 of targets entered vs. those available, and displays it at the end of the game 60 as summative feedback on performance (FIG. 6b).

The Kites game 60 has a score to objectively measure patient's 4 performance:

$$\text{Success } \% * s_{kite} * f_r * \left(\frac{100}{100 - d_f}\right) * (1.2 \text{ if bimanual})$$

In this game, the success rate, given by the percentage of rings caught 68, is multiplied by the redefined parameters, kite 61 speed ($S_{kite}$) and ring 64 frequency ($f_r$=number of rings per unit time), as each parameter works to increase the difficulty of the game 60. The term in parentheses considers the fog density ($d_f$), applying a higher multiplier for denser fog 66. Since all parameters other than success rate are predefined at the start of the game 60, the final score is directly proportional to the number of rings 64 hit. Finally, a 20% bonus is granted for bimanual mode so to account for increased difficulty that introduces new sources of error (hitting the ring 64 with the wrong kite 61).

Figure 7A:
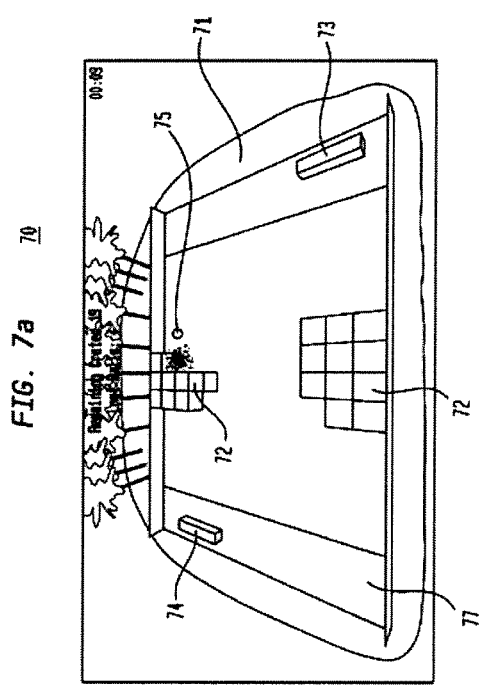
FIG. 7a illustrates a Breakout 3D game in bimanual mode which trains split attention and dual-tasking in an orientation corresponding to predominantly in-out arm movement.

The Breakout 3D game 70 is a bimanual adaptation of the game developed earlier by Burdea's group for uni-manual training on the Rutgers Arm system. See Reference 15. The scene (FIG. 7a) depicts an island 71 with an array of crates 72 placed in a forest clearing. Two paddle avatars 73, 74 of different color, each controlled by one of the patient's hands 17 are located on each side of the crates 72. The patient 4 needs to bounce a ball 75 with either paddle 73, 74, so to keep it in play, and attempt to destroy all the crates 72. The ball 75 is allowed to bounce off several crates, destroying one crate 72 at each bounce. This is the preferred implementation when cognitive training is the primary focus of the game 70. If motor retraining is the primary focus of the game (such as for patients 4 post-stroke) then the ball 75 is allowed to destroy only one crate 72 after each bounce off the paddle avatar 73 or 74. This insures increase arm 22 movement demands corresponding to a given number of crates 72 to be destroyed. The sound of waves is added to help the patient 4 relax. The difficulty of the game 70 is modulated by the speed of the ball 75, the size of the paddles 73, 74, and the number of crates 72 to be destroyed in the allowed amount of time.

Figure 7B:
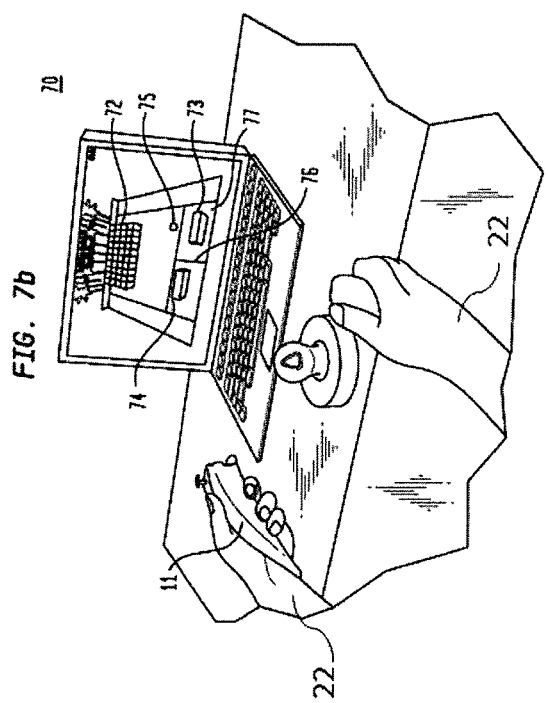
FIG. 7b illustrates Breakout 3D game in bimanual mode which trains split attention and dual-tasking in an orientation corresponding to predominantly left-right arm movement.

In a different version of the Breakout 3D game 70, the paddle avatars 73, 74 are close to the patient 4, and the crates 72 are further away. In this version of game 70 the predominant arm 22 movement is left-right (FIG. 7b). In this configuration a fence 76 is located at the middle of the court 77, so to prevent one paddle avatar 73, 74 from entering the other avatar's space. This features insures that the patient 4 uses both arms 22 to play the game 70. The score for Breakout 3D is given by:

$$\text{crates hit} * \left(\frac{v_{ball}}{l_{paddle}}\right) * \left(\frac{1}{\log(\text{lost balls} + 2)}\right) \qquad (2)$$

The number of points awarded for each destroyed crate 72 is dependent not only on the preset parameters Ball_speed ($v_{ball}$) and Paddle_length ($l_{paddle}$), but also on the number of balls 75 lost. Since the logarithm is an increasing function, there is always a penalty for losing balls 75. Yet, as more balls 75 are lost, the penalty increases at a progressively slower rate, enabling players 4 of lesser skill to achieve better scores. The number 2 is added to prevent divide-by-zero issues (in case no balls 75 were lost).

Games to Train Memory

The first memory game is Card Island, 80 (FIG. 8), again a bimanual version of the game previously used in uni-manual training on the Rutgers Arm system. The patients 4 are presented with an island 81 and an array of cards 82 placed face down on the sand 83. The array of cards 82 is divided symmetrically by a central barrier 84, such that each hand avatar 19 has to stay on its half of the island 81. When a hand avatar 19 overlaps a card 82, the patient 4 can turn it face up by squeezing the Hydra pendant trigger 13. Once a card is turned, a voice recites the name of the card image. The task is to take turns turning cards 82 face up so to find matching pairs. Since non-matching cards 82 turn face down again, the patient 4 has to remember where a given card 82 had been seen before, something that trains short term visual and auditory memory. Once a card 82 had been seen, its back changes color, which is a cognitive aide to the patient 4. The difficulty of game 80 is proportional with the number of cards 82 in the array, and the allowed length of time to find all card pairs.

Card Island is scored by:

$$\left(\text{Correct matches} - \frac{\text{Errors}}{2}\right) * \left(\frac{\text{Deck Size}}{\log(\text{Playtime})}\right) \qquad (3)$$

An incorrect match deducts points equal to half of a correctly matched pair. This allows player 4 a second chance to correct his or her mistake. Leniency is granted towards slower players 4 as exhibited by the logarithm of their playtime measured in seconds. At the same time, this leniency is also depending on the starting deck 82 size. Lastly, no performance bonus is given for bimanual play mode, as the difficulty of this game lies in the player's 4 short-term visual and auditory memory abilities.

Remember this card, 90 (FIG. 9a) is a game that trains long-term visual and auditory memory. The game consists of two parts 91, 92, interspaced by other games. In the first part 91 the patient 4 is presented with a number of cards 93 placed face down. Each card needs to be turned face up, at which time a sound in played associated with the image on the card. For example, if the card 93 depicts a phone booth 94, then a ring tone 95 in played. After all cards 93 had been explored, the patient 4 selects one, by flexing the hand avatar 19 over the card, and is prompted with the "Remember this card" text. After a number of other games are played, the second part of the game 92 appears, with a scene that shows the cards 93 previously explored, this time lined up face up. Patient 4 is asked to select the card he had been asked to remember before. If the attempt is unsuccessful, the "Oups, nice try!" text 95 appears (FIG. 9b), otherwise the patient 4 is congratulated for remembering correctly. The difficulty of the game 90 is modulated by the number of card choices 93, as well as the number of other games interposed between the two parts 91, 92 of this delayed recall game 90.

The score is:

$$\frac{50 * \text{Number of Cards}}{\log(\text{Recall time} + 2)} \qquad (4)$$

The score scales linearly with the number of cards 93 while being more lenient on the time taken to recall and choose the correct card. The recall time is the time taken by the patient 4 to pick their previously selected card among those shown, measured in seconds. For any given number of cards 93 in this formula, a player 4 who takes less time to choose the correct card will always receive a higher score than a slower player. However, the slower players will not see a larger gap in scores, regardless of how long they take to remember the original card. Again, 2 (measured in seconds) is added to the recall time in order to prevent divide-by-zero errors.

Game to Train Executive Function

Tower of Hanoi 3D game, 110 is similar to the version of the game being played with a mouse online. The patient 4 has to restack a pile of disks 111 of different diameters, from one pole 112 to another pole 113, using a third pole 114 as way-point. The game 110 trains decision making/problem solving by setting the condition that no larger disk 111 can be placed on top of a smaller diameter one.

Figure 10:
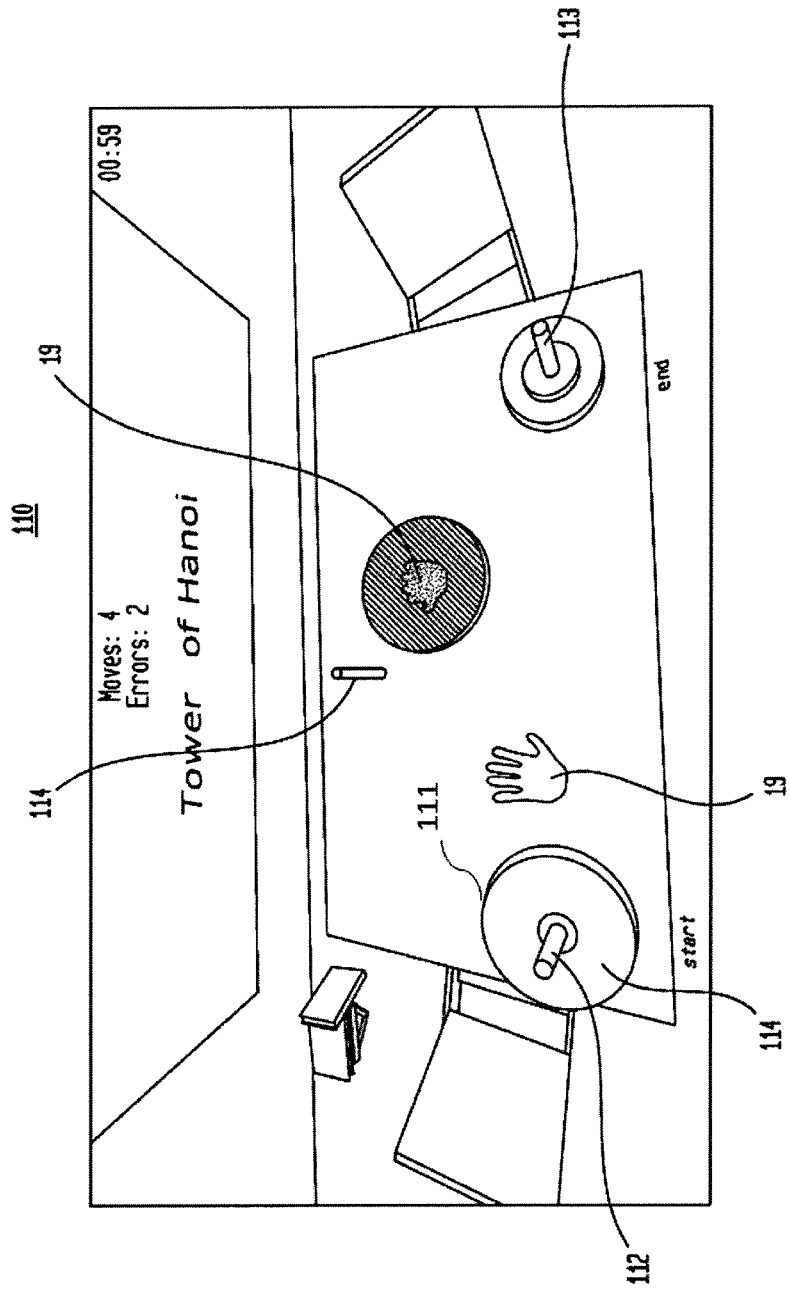
FIG. 10 illustrates the use of the Tower of Hanoi 3D game to train executive function wherein two hand avatars are allowed to only manipulate like-colored disks when restacking them on the target pole.

In the version of the game 110 for bimanual therapy, the scene shows two hand avatars 19, one green and one red and similarly colored red and green disks 111 (FIG. 10). Each hand avatar 19 is allowed to manipulate only disks 111 of similar color. The game 110 chooses randomly the green or the red color for the smallest disk and allocates the other color to the other disks. In this configuration, both hands 17 are doing approximately the same number of moves. The difficulty of the game 110 depends on the number of disks 111 (2—easy, 3—medium, 4—difficult). The number of moves in the game 110 is counted and compared to the ideal (smallest) number of moves to complete the task. Thus cognitively, achieving an economical (minimal) number of moves to solve the problem is indicative of good problem solving skills.

The score is:

$$\frac{150 * \text{disks} * (1.2 \text{ if bimanual})}{\log(\text{moves} - \text{pow}(2, \text{disks}) + 3) * \log(\text{Playtime})} \quad (5)$$

If a patient 4 was unable to complete the game 110, we assign a flat score of 100, so to maintain patient 4 motivation. In this game, each disk 111 is worth 150 points, with 20% increase in bimanual play mode to account for the increased difficulty and newly introduced sources of error. This number is countered by a product of logarithms (for leniency): the first compares the number of moves made by the patient 4 against the optimal solution, and the second factors in the time taken to solve the task.

Dual Tasking and Therapy Gradation

As stated before, dual tasking is typically problematic with older populations (whether stroke survivors or not). Thus some of the games have embedded dual-tasking features, notably Breakout 3D 70. When the dual tasking parameter is set, the paddle avatar 73, 74 characteristics depend on whether the trigger 13 is squeezed during movement or not. When a momentary squeeze is required, the patient 4 has to squeeze the trigger 13 at the moment of bounce, lest the ball 75 passes through the paddle 73, or 74 and is lost. When a sustained grasp is required, the movement of the paddle 73, 74 is decoupled from that of the pendant 11 when the trigger 13 is not squeezed. Thus the patient 4 has to remember to keep squeezing to move the paddle 73, 74 to bounce the ball 75. Recognizing that sustained squeezing may be fatiguing and may induce discomfort for some patients 4, the game 70 sets a threshold as a % of range when classifying an index 18 flexion as a squeeze. This threshold is based on the finger 18 flexion baseline 40 previously described (FIG. 5).

Naturally, the introduction of the squeezing requirement further increases game 70 difficulty. Thus the weeks of therapy are gradated in terms of session duration and game difficulty. The approach in this application is to begin with shorter sessions of 30 minutes in week 1, progress to 40 minutes in week 2 and 50 minutes for the remaining weeks. The games in week 1 are uni-manual, so to familiarize the patient 4 with the system 100 and its games 1. Gradually the games 1 difficulty is increased, switching to bimanual mode in week 2 or later, and in the last 3 weeks the dual tasking condition is introduced. The aim is to always challenge the patient 4, offer variety, but make games 1 winnable, so to keep motivation high.

Arm 22 and Index Finger 18 Repetitions 120

It is known in the art that the amount of movement repetitions 120 within a task is crucial to induce brain plasticity. Within the system 100 described here the tasks are dictated by the different games 1, and the system 100 measures the number of repetitions 120 during play. The number of repetitions 120 is arm specific, as well as index finger 18 specific (right, left), and is summed for the session, by totaling the repetitions of each game 1. The amount of repetitions 120 is an indication of endurance, while the intensity of play is expressed by repetitions in unit of time. Arms endurance and therapy intensity are useful tools for the therapist.

Figure 11:
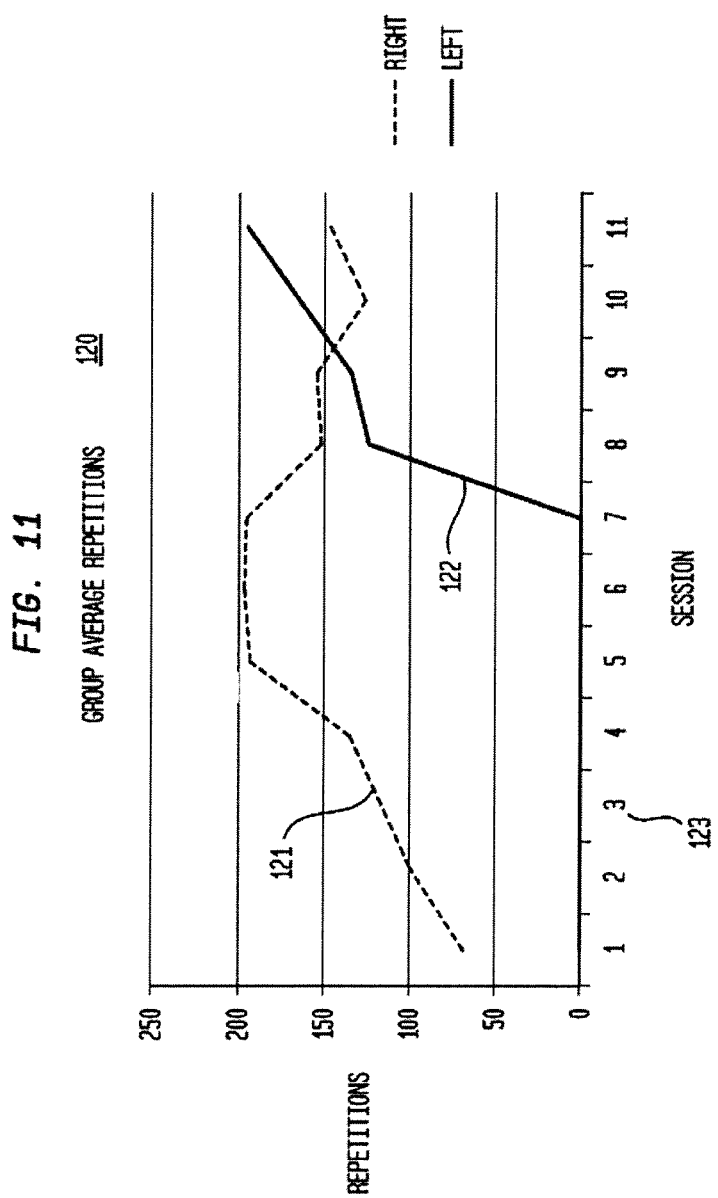
FIG. 11 shows a graph depicting average right and left arm repetitions during group training over a sequence of sessions.

In group therapy the repetitions 120 may be averaged over the group of patients 4 for a given session. FIG. 11 depicts a graph showing the left and right arm 22 number of repetitions 121, 122 over a sequence of sessions 123. It can be seen that over the first 7 sessions the right arm number of repetitions 121 grows, while the left arm 22 is motionless. This is due to the fact that during these 7 sessions the games 1 were played in uni-manual mode, and thus only one arm was used. The reason the number of repetitions 121 increases for right arm 22 is the increased session duration, implying more games played. Once the games 1 started being played with both arms 22, it can be seen that the left arm 22 has a steep increase in its number of movement repetitions 122, while the right arm number of repetitions 121 is somewhat reduced. Eventually both arms share about equally in the game play.

At each session the average arm repetitions value for the group is associated with a standard deviation. Standard deviation visualizes the span of total repetitions values for each member in the group as measured in a given session 123. Typically, the standard deviations are larger at the initial sessions and smaller for later sessions. This is indicative of increased uniformity of effort among group members for later sessions.

Discussion

A pilot feasibility study took place with two elderly participants who were in the chronic phase of stroke and had arm/hand spasticity (See Reference 16).

The pilot feasibility study aim was to determine technology acceptance as well as any clinical benefits in the cognitive and emotive domain of training on the BrightBrainer™. These were measured by a blinded neuro-psychologist consultant using standardized tests. Results showed excellent technology acceptance and benefits to the two patients 4 in various cognitive domains. One patient had reduced depression following the therapy.

Subsequently a larger study with 10 elderly nursing home residents took place in summer 2013. See reference 17. Eight of the participants 4 had dementia and one had severe traumatic brain injury. They played the games described above and three other games we developed. The new games were: Pick-and-Place bimanual 130, Xylophone bimanual 140, and Musical Drums 150, bimanual.

Figure 12:
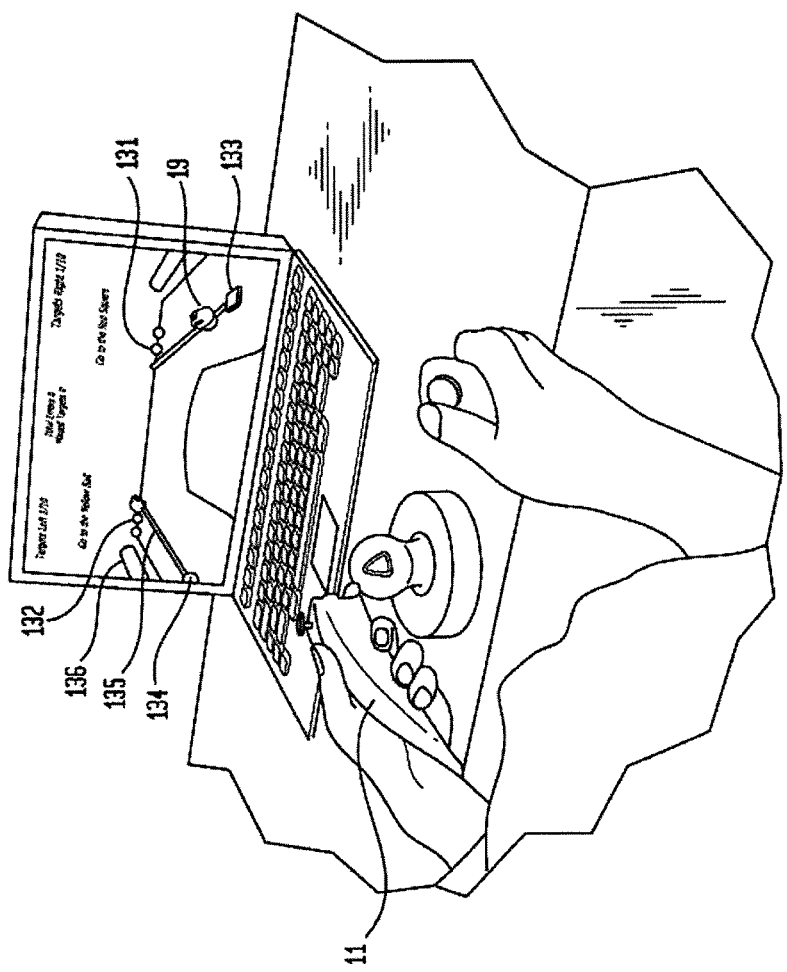
FIG. 12 illustrates a Pick-and-Place bimanual game.

The Pick-and-Place game 130 bimanual (FIG. 12) depicts two hand avatars 19 that need to pick a ball 136 each from three possible choices 131, 132 and move them to target areas 133, 134 following prescribed (ideal) paths 135. Each time a ball 136 is correctly moved to a target 133, 134, a different sound is played. The patient 4 has a choice of moving one arm controlling on hand avatar 19 holding a ball 136 at a time or of moving both arms 22 at the same time (a more difficult task). The game 130 difficulty depends on the number of required repetitions, and errors are counted whenever the wrong ball is picked up. The Pick-and-Place game trains hand-eye coordination and dual tasking may be introduced by requiring the patient to squeeze the Hydra trigger 13 to keep the ball 136 grasped by hand avatar 19.

In the Xylophone game 140 (FIG. 13) the patient 4 controls two hammer avatars 141, and needs to hit keys 142 to create a sound (play a note). The patient 4 is tasked with reproducing sequences of notes by playing the instrument keys 142 in the correct order. The difficulty of the game depends on the length of note sequences to be reproduced, as well as the total amount of time available to complete a series of note sequences.

Another game is Musical Drums 150 (FIG. 14) where the patient 4 needs to hit notes 151 scrolling on the screen with a hammer avatar 141 when the notes 151 overlap a drum 152 to get points. The difficulty of the game 150 increases with the tempo of the song 153 being played, corresponding to faster scrolling of the notes 151 across the screen. Further increase in difficulty occurs when notes scroll across more drums 152.

Patients had to play the games two times per week for 8 weeks. To measure clinical benefit, standardized tests were done by a blinded neuropsychologist before and after the 8 weeks of therapy. These tests showed statistically significant group improvement in decision making capacity, and borderline significant reduction in depression.

In summary, one aspect of the present invention is to provide a method of providing therapy to a patient having a first arm, a first hand, a second arm and a second hand. The method includes executing a video game on a computer and portraying action from the video game on a display, the action being viewable by the patient; the patient holding a first component of a game controller in the first hand and manipulating an interface on the first component of the game controller with the first hand and moving the first component of the game controller with the first hand and the first arm to control the video game; the patient holding a second component of a game controller in the second hand and manipulating an interface on the second component of the game controller with the second hand and moving the second component of the game controller with the second hand and the second arm to control the video game. The first component of the game controller is separate from the second component of the game controller and can be moved independently from the second component of the game controller. The game controller sends one or more signals representative of a position of the interface on the first component, of a position of the interface on the second component, of a motion of the first component and of a motion of the second component are reported by the game controller to the computer; and the computer analyzes the one or more signals and controlling the video game to control action portrayed on the display.

The video game can also control the computer to cause a displayed object to include one of two codes wherein a first code indicates that the displayed object can be moved with the first component of the controller and a second code indicates that the displayed object can be moved with the second component of the controller. Preferably, the two codes are different colors.

While the game is played the computer monitors and stores a set of information from the first component and the second component of the controller. The set of information includes: activation of the interface (button and trigger) on the first component of the controller; movement of the first component of the controller; activation of the interface on the second component of the controller; and movement of the second component of the controller.

The computer controls the video game and resulting action on the display in accordance the set of information. The computer also analyzes the set of information to determine progress of the patient. In one embodiment of the present invention, the computer controls the action displayed such that the action caused by the first component of the controller is the same as the action caused by the second component of the controller even if one of the arms is impaired and does not perform as well. As explained before, extra oxygen can be fed to the patient from an oxygen tank while the patient manipulates the first component and the second component. Also as explained before the patient can wear wrist weights on the first arm, on the second arm or on both arms while the patient manipulates the first component and the second component. Alternatively, weights can be added to either the first component of the game controller, to the second component of the game controller or to both. The handheld components can be modified to have the weights attached to them. The values of the two weights need not be the same for the two arms.

In accordance with an aspect of the present invention, the computer controls a videogame avatar object in response to activation of the interface (button and/or trigger) on each of the handheld components of the controller. The avatar object can be controlled by movement of each handheld component of the controller. Alternatively, one avatar object can be controlled by the movement of the first (say the left) handheld component while another avatar object can be controlled by the movement of the second (say the right) handheld component. Thus, a computer can control a videogame avatar object to respond to movement of the first component of the controller if the button or the trigger on the first component are pressed and the computer controls another video game avatar object to respond to movement of the second component of the controller if the button or the trigger on the second component are pressed.

A system of providing therapy to a patient having a first arm, a first hand, a second arm and a second hand, is also provided as explained above.

Figure 15A:
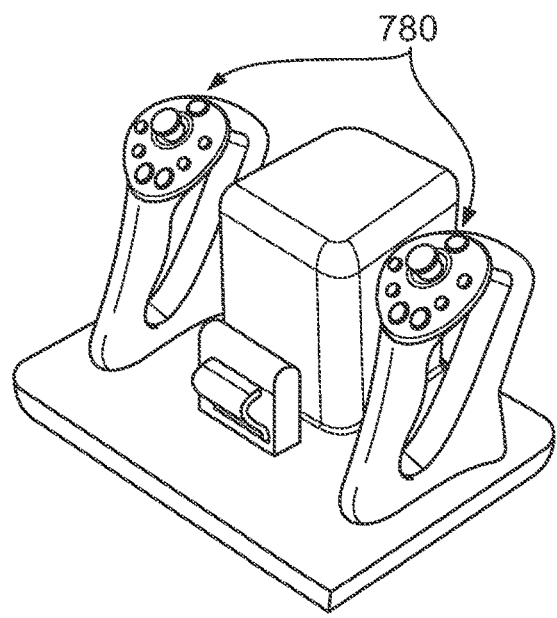
FIG. 15a illustrates a controller according to one embodiment of the present invention.
Figure 15B:
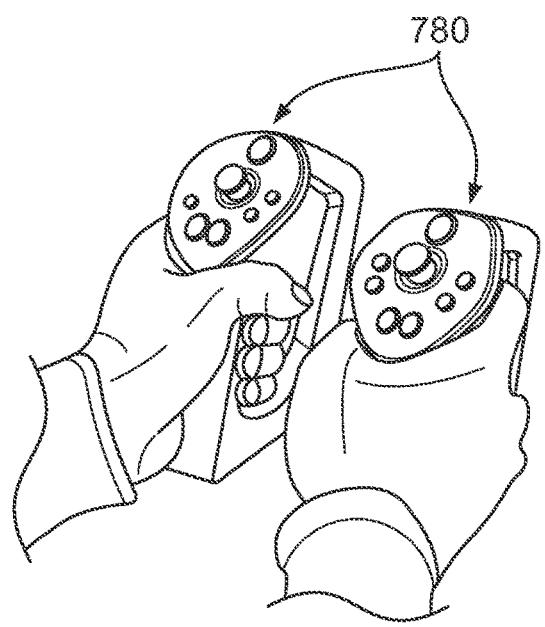
FIG. 15b illustrates wireless hand-held pendants according to one embodiment of the present invention.
Figure 15C:
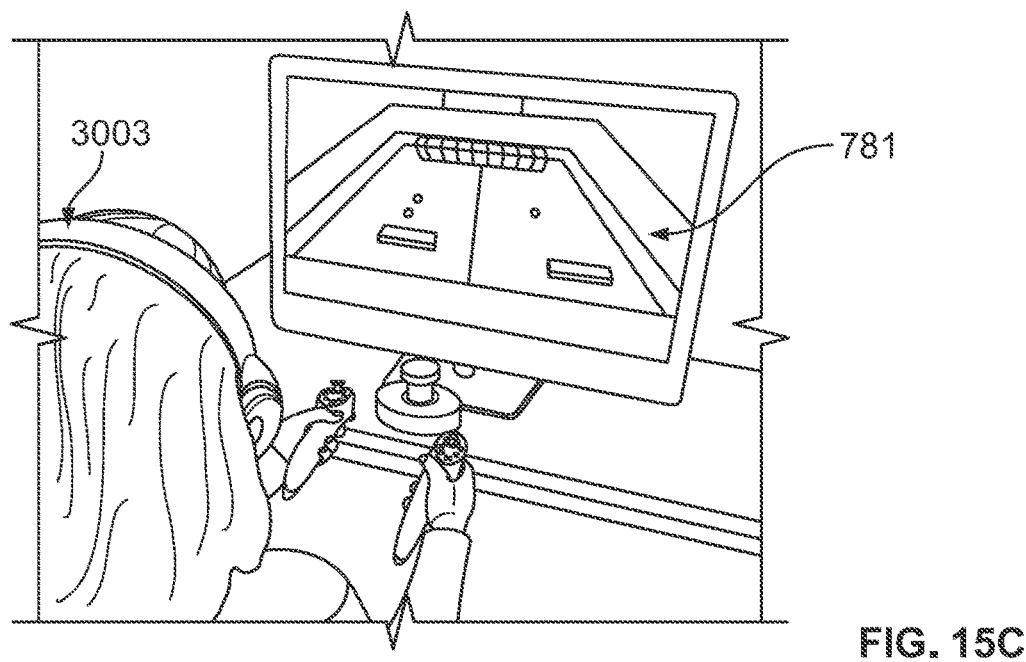
FIG. 15c illustrates an all-in-one PC as one embodiment of the present invention.

In accordance with another aspect of the present invention, a screening software and method of evaluation/triage may be used with the hardware described above for cognitive screening, which has the commercial name BrightScreener™. In one embodiment of the invention, BrightScreener is a portable (laptop-based) serious-gaming system which incorporates a bimanual game interface for more ecological interaction with virtual worlds. It is envisioned that BrightScreener may use wireless bimanual interfaces 780 such as the STEM system developed by Sixense Entertainment (Reference No. 25) (FIG. 15) or similar interfaces.

In another embodiment of this invention BrightScreener software may run on an all-in-one touch-sensitive PC, 781, and sound may be played on headphones 3003 so to better insulate the person being screened from distracting surrounding sounds.

Figure 16:
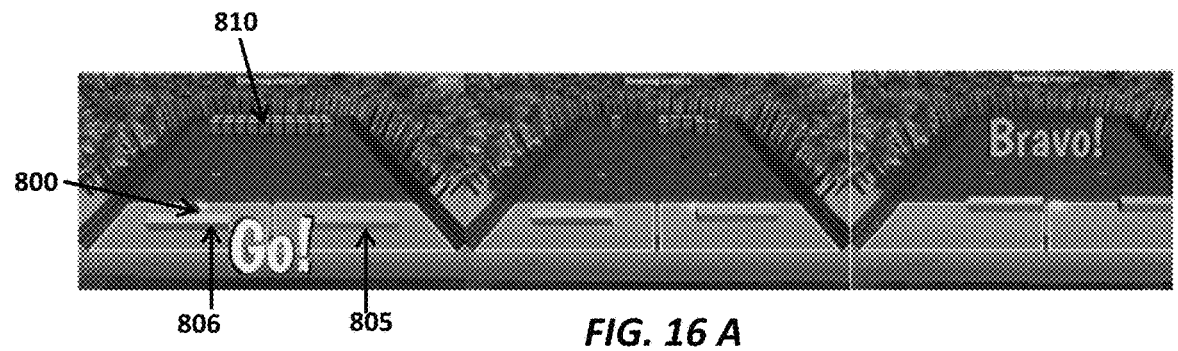
FIG. 16a illustrates a BrightScreener game according to one embodiment of the present invention.
FIG. 16b illustrates another BrightScreener game according to one embodiment of the present invention.
FIG. 16c illustrates another BrightScreener game according to one embodiment of the present invention.
FIG. 16d illustrates another BrightScreener game according to one embodiment of the present invention.
Figure 16:
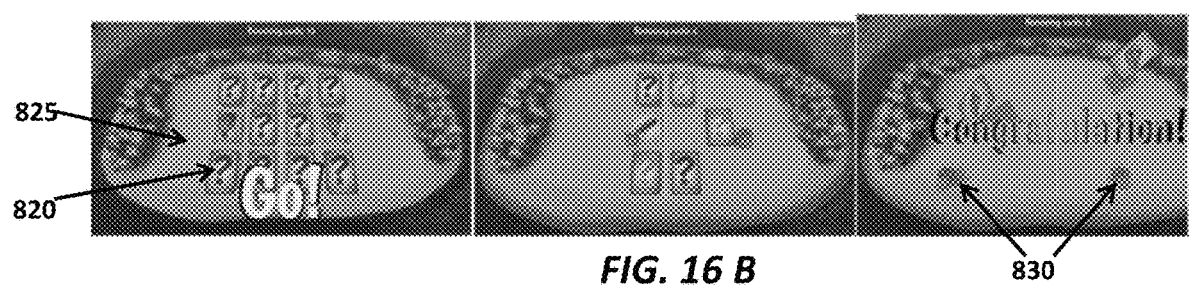
Figure 16:
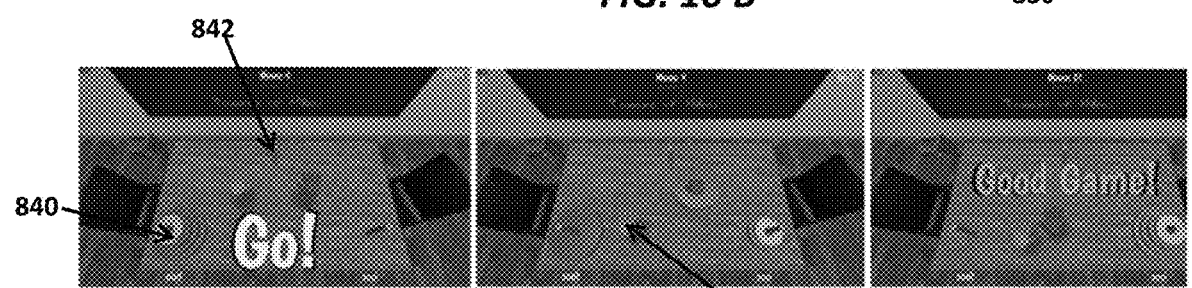
Figure 16:
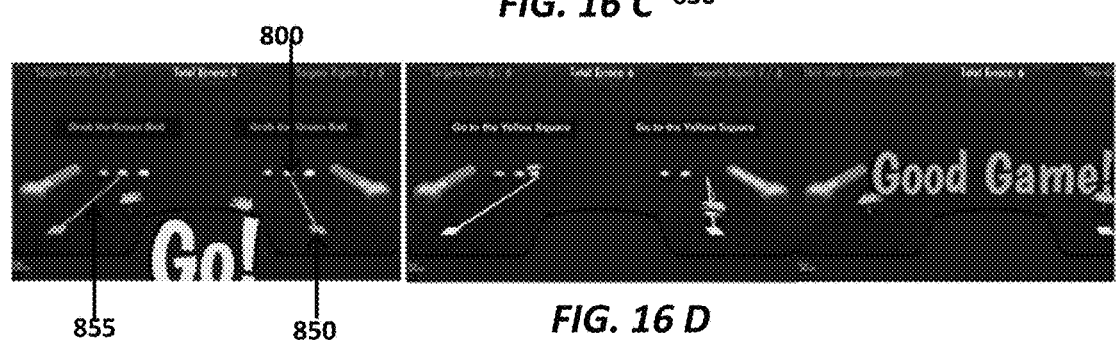

The games used by BrightScreener may be cognitive-domain specific, some games training short-term visual and auditory memory, others focusing, others divided attention, or problem solving/executive function. A combination of these games targeting different domains should cover a breadth of cognitive areas, analogous to how cognitive paper and pencil tests contain groups of questions that target different mental indicators. A sample of select games to develop a comprehensive, non-hearing and speech-based cognitive screening is shown in FIG. 16 (Reference No. 29).

Breakout 3D (FIG. 16a) asks subjects to bounce balls 800 alternating between right peddle 805 and left peddle 806 avatars, so to destroy rows of crates 810 placed on an island. The game tests executive function through reaction time (processing speed) and task sequencing, as well as attention.

Card Island (FIG. 16b) asks subjects to pair cards 820 arrayed face down on the sand 825. Hand avatars 830 are used to select and turn cards 820 face up (two at-a-time) when a pendant trigger button is pressed. The placement of the game on an island integrates the sound of waves, so to further relax the subjects. The Card Island game tests short-term visual and auditory memory and attention.

Tower of Hanoi 3D (FIG. 16c) is a Bright Cloud International version of a well-known cognitive game, normally played online with a mouse. The subject is asked to restack disks 840 of varying diameters from one pole 842 to another pole 842, using the third pole 842 as a way-point. The complexity of the task stems from the requirement that a larger disk may never be placed on top of a smaller one. A disk is picked up by overlapping it with a hand avatar 830 and squeezing the trigger to flex the hand fingers. In bimanual mode there are two hand avatars, one colored green and one red, and disks are similarly colored. Each hand avatar can only manipulate like-colored disks. The game tests executive function (task sequencing and problem solving).

Finally, in Pick and Place (FIG. 16d) the subject has to pick up a ball 800, from several available, and place it on a like-colored target square 850. While in route to the target the movement of the hand avatar is traced 855. The game tests working memory and divided attention when played in bimanual mode. Other games have been envisioned as part of BrightScreener system.

Each game used by BrightScreener may have several levels of difficulty, with the most basic setting utilizing one hand controller (uni-manual mode). The remaining levels may require both hand controllers to play (bimanual mode). At successive levels, Breakout 3D, for example, may become more difficult with increase in the speed of the ball and decrease in the size of the paddle avatars used to bounce it. Card Island may become more complex by increasing the number of cards to be paired. Similarly, the number of disks in Tower of Hanoi 3D increases with successive difficulty levels (two disks, then three, then four disks and so on). Pick and Place increases difficulty with the increase in number of targets and the removal of visual cues used by subjects to match ball and target colors and complete the pick and place task.

When subjects are new to BrightScreener, it may be beneficial to have a tutorial session before the actual cognitive evaluation session. During a tutorial session subjects play the games (such as those previously described) and each game may be played several times at progressively harder levels of difficulty. The subjects may cycle through all games at the most basic level of difficulty before progressing to the next level of each game type, and so on. In alternate configurations, subject may play the same game multiple times in succession before progressing to a different game. Additionally, the level of difficulty in successive instances of playing a game may be based on the performance of previous instances of playing that game. Furthermore, the level of difficulty may progress or regress depending on performance during the course of continuous play of a game.

For the cognitive testing session, similar to a tutorial session, a subject may play the same game multiple times in succession before progressing to a different game; the level of difficulty in successive instances of playing a game may be based on the performance of previous instances of playing that game; and the level of difficulty may progress or regress depending on performance during the course of continuous play of a game.

During game play for testing, BrightScreener may capture actions or events during game play based on the subject's interaction with the game. For example, one such metric may be the amount of time to complete a goal within the game or the number of times a game objective was missed (such as hitting a virtual ball with a virtual paddle). In another embodiment, precision of the movement of hand controllers may be recorded over time. As seen in FIG. 17, this may correspond to moving a virtual object 900 such as a ball to a target location 905 (Pick-and-Place above). Each game may be scored based on game specific formulas based on the capture metrics and game difficulty parameters (such as the speed of the ball in Breakout 3D). For each game played, the score assigned may be the average score for multiple difficulty levels for that game. A composite testing score may be formulated from the weighted combination of scores captured for different types of games.

The overall testing session score may then be used to place the individual in one of several cognitive "bands". These may be "normal", "mild cognitive impairment (MCI)," "moderate cognitive impairment", and "severe cognitive impairment."

Figure 18A:
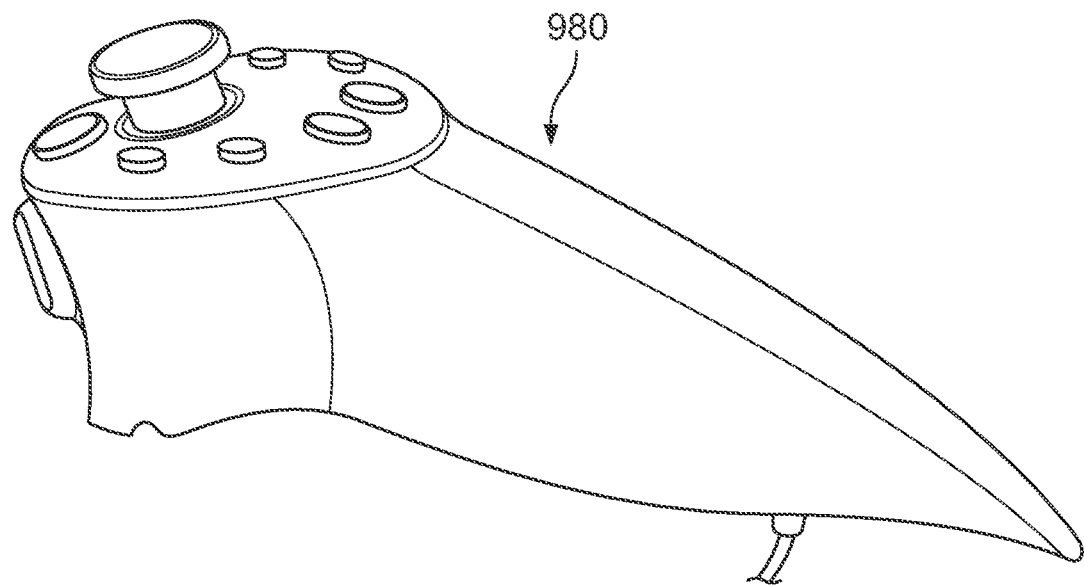
FIG. 18a illustrates a game interface according to one embodiment of the present invention.
Figure 18B:
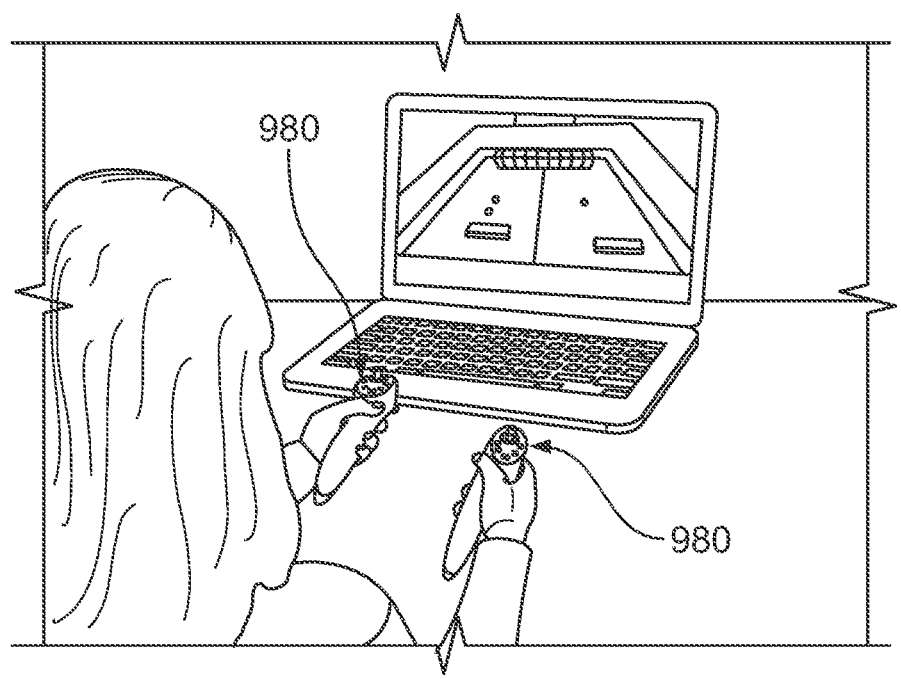
FIG. 18b illustrates a subject operating a game according to one embodiment of the present invention.

In one or more embodiments, BrightScreener is laptop-based, and portable. As seen in FIG. 18, the system hardware may incorporate a Razer Hydra bimanual game interface (Reference No. 41), allowing the subject to interact with the custom simulations. The Hydra pendants 980 are light, intuitive to use and track full arm movements in real time. In addition they measure the degree of index flexion-extension, which combined with the tracking feature allow the creation of dual tasking scenarios.

In one or more embodiments, BrightScreener may be comprised of several games that were ported from Bright-Arm (see Reference No. 38) and re-written in Unity 3D (Reference No. 41). Furthermore, all games may be made to have uni-manual and bimanual modes, with game avatars controlled through the Hydra pendants. As described below, four of the games were selected for the BrightScreener cognitive evaluation feature. These games were Breakout 3D, Card Island, Tower of Hanoi 3D and Pick-and-Place.

Data

In accordance with an aspect of the present invention, BrightScreener was tested as a screening system for individuals with dementia, including a person with Alzheimer's disease (See Reference No. 23). BrightScreener was used for evaluating elderly with various degrees of cognitive impairment to evaluate the technology acceptance by the target population and to determine if BrightScreener is able to differentiate levels of cognitive impairment based on game performance.

Eleven subjects were recruited by the study Clinical Coordinator, from the pool of potential participants at MECA. Of these five were women and six men. Subjects 1-5 were tested the first Saturday and Subjects 6-11 were tested a week later. The group had an average age of 73.6 years, with a range from 61 to 90 years old and a standard deviation of 8.6 years. The mean education level was 14.5 years in school, with a standard deviation of 4.2 years.

Since subjects were new to BrightScreener, it was necessary to have a tutorial session before the actual cognitive evaluation session. During the tutorial session subjects played the four games previously described, and each game was played at progressively harder levels of difficulty. The subjects cycled through all four games at the most basic level of difficulty before progressing to the next level of each game type, and so on. The tutorial session lasted about 35 minutes per subject.

For testing, the subjects completed the four levels of difficulty of a given game before proceeding to the next game, and so on. The evaluation session lasted about 30 minutes per subjects.

The sequence of steps used in this study consisted of (1) subject consenting, (2) a tutorial session on the BrightScreener, followed by (3) standardized cognitive testing, then (4) the game-based testing session and (5) an exit questionnaire. Each subject completed the study in the span of a few hours (depending on their cognitive functioning level). The study was approved by the Western Institutional Review Board and took place during two days at the Memory Enhancement Center of America—MECA (Eatontown, N.J.) in February 2014.

Subjects first underwent clinical scoring with the standardized MMSE test. During the same visit they underwent a BrightScreener familiarization session and then an evaluation session on the device. At the end of their visit, each subject filled a subjective evaluation exit form. Technologists were blinded to MMSE scores known only to the clinical coordinator who had administered the MMSE. Subsequent group analysis of BrightScreener data using the Pearson correlation coefficient showed a high degree of correlation between the subjects' MMSE scores and their BrightScreener Composite Game Scores (0.90, I P1<0.01).

The scoring equation for each game incorporated both difficulty and performance metrics. For example, a 25% bonus was given for increased difficulty when playing bimanually over uni-manual version of the same game. Play time was typically used to rate game performance. For example, the score formula for Tower of Hanoi 3D was:

$$\text{Score} = \frac{(\text{If bimanual } 1.25; \text{else } 1.0;) * (\text{Minimum\# of Moves}) * 100}{\text{Log(Time in Seconds)} * (\text{Actual \# of Moves} + \text{\# of Dropped Disks})} \quad (6)$$

In the numerator, level of difficulty is quantified by whether the game is played in bimanual mode (25% bonus) and minimum number of moves needed to complete the game. Restacking 2 disks required a minimum of 3 moves, 7 moves were necessary to restack 3 disks and 15 moves for 4 disks. In the denominator, game performance was quantified by the logarithm of game completion time and the actual number of moves taken to complete the game combined with the number of disks dropped en route to the poles. Longer length of game play (measured by time and number of steps) corresponds to lower performance and hence has a lower game score.

Table 1, below, shows the subject's characteristics by gender, age, and education level.

TABLE 1

| Subject # | Gender | Age | Years in School |
|---|---|---|---|
| 1 | M | 64 | 16 |
| 2 | M | 73 | 19 |
| 3 | M | 82 | 22 |
| 4 | F | 90 | 14 |
| 5 | M | 73 | 18 |
| 6 | F | 77 | 12 |
| 7 | M | 78 | 14 |
| 8 | F | 70 | 14 |
| 9 | F | 61 | 12 |
| 10 | F | 64 | 13 |
| 11 | M | 78 | 6 |

Average Age = 73.6 (8.6)
Average School years = 14.5(4.2)

Subject's data was collected during the study using MMSE, game scores, and an exit interview. Mini Mental State Exam was used to evaluate the subject's cognitive function. The MMSE was administered by the Clinical Coordinator in a quiet room and the BCI researchers were blinded to the scores.

Subsequent to the MMSE testing, subjects were given the BrightScreener evaluation session and game scores stored transparently for each subject. Finally, the subjects filled a subjective evaluation exit form in the Clinical Coordinator room. The form had 8 questions scored on a Likert scale from 1 (least desirable outcome) to 5 (most desirable one). The questions were: "Were instructions easy to understand?," "Were the games easy to play?," "Were the game handles difficult to use?," "How easy was playing with one hand?," "How easy was playing with both hands?," "Were you tired after playing the games?," "Did you have headaches after playing the games?," and "Did you like the system overall?"

Table 2, below, lists the MMSE scores and cognitive impairment level of the 11 study subjects.

TABLE 2

| Subject # | MMSE Score | MMSE Rank | Cognitive Impairment Level |
|---|---|---|---|
| 1 | 29 | 1 | Normal |
| 2 | 24 | 7 | Mild |
| 3 | 25 | 5 | Mild |
| 4 | 9 | 11 | Severe |
| 5 | 27 | 3 | Normal |
| 6 | 29 | 1 | Normal |
| 7 | 26 | 4 | Mild |
| 8 | 24 | 7 | Mild |
| 9 | 23 | 9 | Mild |
| 10 | 25 | 5 | Mild |
| 11 | 22 | 10 | Mild |

These scores ranged from a low of 9 to a high of 29 (out of a maximum of 30). The average MMSE score was 23.9 with a standard deviation of 5.4. Based on their MMSE scores, participants were ranked by degree of cognitive impairment from 1 (the least) to 11 (the most). Subjects with identical scores (1 and 6, 2 and 8) were given the same rank (1 or 7, respectively).

The MMSE scores may be used to determine the degree of cognitive impairment (Reference No. 31). Three of the subjects were classified as having normal cognitive function, seven of the subjects were diagnosed with Mild Cognitive Impairment (MCI) and one with Severe Cognitive Impairment (Alzheimer's). For control, at least one participant that was expected to have a normal diagnosis was included in each day of the study. However, the identities of these individuals were not known by technologists conducting the game training and game-based cognitive screening sessions.

Table 3, below, summarizes the game scores and corresponding ranking during the testing session.

TABLE 3

| Subject | Breakout Score | Card Island Score | Pick & Place Score | Towers Score | Composite Score | Composite Rank | Cognitive Impairment Level |
|---|---|---|---|---|---|---|---|
| 1 | 78.8 | 43.3 | 37.1 | 74.3 | 58.4 | 3 | MCI |
| 2 | 51.9 | 49.9 | 52.0 | 86.9 | 60.2 | 2 | Normal |
| 3 | 64.7 | 53.5 | 36.9 | 70.5 | 56.4 | 5 | MCI |
| 4 | 18.3 | 5.4 | 0.0 | 0.0 | 5.9 | 11 | Severe |
| 5 | 69.9 | 53.6 | 46.1 | 75.5 | 61.3 | 1 | Normal |

TABLE 3-continued

| Subject | Breakout Score | Card Island Score | Pick & Place Score | Towers Score | Composite Score | Composite Rank | Cognitive Impairment Level |
|---|---|---|---|---|---|---|---|
| 6 | 39.7 | 41.0 | 36.1 | 76.8 | 48.4 | 8 | MCI |
| 7 | 56.1 | 56.8 | 38.9 | 77.6 | 57.3 | 4 | MCI |
| 8 | 46.7 | 49.6 | 32.5 | 55.6 | 46.1 | 9 | MCI |
| 9 | 58.6 | 57.6 | 42.4 | 57.9 | 54.1 | 7 | MCI |
| 10 | 61.2 | 60.8 | 23.5 | 71.6 | 54.3 | 6 | MCI |
| 11 | 83.4 | 26.8 | 26.6 | 20.4 | 39.3 | 10 | MCI |

For each of the 4 games played, the score assigned was the average score for four difficulty levels of each game. Participant 4 consistently scored the lowest across games, however the participant with the highest score varied between games. In order to realize an overall ranking, each participant's scores were averaged into a Composite Score. Subject 4 had the lowest composite score (5.9) and Subject 5 the highest composite score (61.3).

Subsequently the 11 subjects were ranked from 1 to 11 using the composite game scores. The scores were also categorized into four basic bands following degree of cognitive impairment: normal, mild, moderate, and severe. The thresholds quantizing composite scores to the cognitive impairment levels were calibrated based on the fact that the Clinical Coordinator indicated prior to study that two undisclosed participants were expected to have a normal cognitive state. As seen in Table 3, eight of the participants were categorized as MCI, none of the participants were classified as having moderate cognitive impairment and one participant was categorized has having severe cognitive impairment. This is consistent with the distribution of the MMSE, although individual classifications do vary (i.e. participants 2 and 6).

Table 4, below, shows the Spearman correlation (Reference No. 33) between individual game scores and the MMSE test scores.

TABLE 4

| Correlation | Breakout 3D | Card Island | Pick & Place | Tower of Hanoi | Composite Score |
|---|---|---|---|---|---|
| P | 0.60 | 0.75 | 0.78 | 0.85 | 0.90 |
| P | 0.045 | 0.006 | 0.0037 | 0.00048 | .000008 |

The correlation values ranged from a low of 0.6 for Breakout 3D to a high of 0.85 for Tower of Hanoi 3D, with probability $|P|<0.05$. As seen, the correlation for Breakout 3D was less than for the other games due to the fact that Subject 11 performed particularly well for this game. When Subject 11 was removed from the correlation computation, the Breakout 3D correlation increased to 0.75. This correlation value is now in line with Card Island and Pick and Place correlation values.

The Composite Score correlated to MMSE outcomes better than individual game scores. The correlation value was 0.90 with a confidence $|P|<0.01$. This is reflective of the nature of the individual games, each targeting a different group of cognitive domains. The rationale for using the Composite Score is a broader spectrum of domains may be captured in a single value, similar to the methodology of the MMSE instrument.

The Spearman correlation was subsequently computed between the ranking of subjects using MMSE scores and the ranking of those same subjects based on game scores. The ranking using the composite score had a correlation value of 0.6 and $|P|<0.05$. The Spearman value was higher when ranking by Tower of Hanoi 3D alone with a correlation of 0.69 with $|P|<0.05$. A better Spearman correlation was achieved by limiting the contribution of Pick and Place, correlation value of 0.71 with $|P|<0.05$.

Spearman rank correlation tends to amplify noise in the ordering. This is seen through the fact that the overall correlation value of 0.6 is much lower than the 0.9 found by correlation between composite game scores and MMSE scores. If BrightScreener were to be used as a cognitive function screening tool, it may be sufficient to categorize subjects into 4 general categories (normal, Mild, Moderate and Severe cognitive impairments), as opposed to get exact ordering within particular categories. To this end, the cognitive impairment levels for games scores was correlated with the diagnostic from MMSE test. Here, a much higher correlation value of 0.8 was measured, with a $|P|<0.01$.

The subjects were asked to fill out a subjective questionnaire after completing the game-base testing. Although anecdotal evidence suggested that the subjects rarely played video games, the subjective evaluation response was consistently positive. For example, subjects gave an average rating of 4.8 out of 5 to the question "Were the instructions easy to understand?"

The challenge of playing bimanually was measured through the question: "How easy was playing with both hands?" This received the lowest rating of all questions, namely a 4.1 out of 5. Finally, the subjects were asked "Did you like the system overall." Each of the 11 participants gave the system a perfect rating of 5. All the other questions received a rating of 4.3 to 4.8.

The aims of this pilot study were: 1) to determine if the BrightScreener system was able to differentiate levels of cognitive impairment based on game performance, and 2) to evaluate the technology acceptance by the target population. Virtual reality use in emotive therapy has been tried successfully for a number of years, beginning in the 90s (Reference No. 40). Within the cognitive domain many studies have used virtual supermarkets to train executive function (Reference No. 34), or as a more ecological method for MCI diagnosis (Werner et al., 2009). Researchers tested a group of 30 MCI patients and 30 healthy elderly adults. They observed significant differences in the performance of the two groups in the virtual supermarket simulation. A key differentiation with the prior systems is that BrightScreener uses serious-games as a scoring method for cognitive impairment. The results were shown to be consistent with determination of a popular pencil and paper screening method (MMSE).

BrightScreener interactions were mediated by a bimanual game controller, and the technology was well accepted by the subjects. Another usability study involving an off-the-shelf game interface used the Wii controller with dementia patients (Reference No. 27). Similar to the present study, researchers found that subjects were able to use the Wii and liked the technology very much.

Despite the small sample size, results suggest that serious-gaming strategies can be used as a digital technique to stratify levels of Cognitive Impairment. The above results are supportive of the idea that a computerized system using bimanual game interfaces may be an alternative to conventional standardized scoring for Mild Cognitive Impairment and Dementia.

The following is a list of references referred to herein, each of which is incorporated by reference:

Reference No. 1—Roger V L, Go A S, Lloyd-Jones D M, Benjamin E J, Berry J D, Borden W B, et al. Heart disease and stroke statistics—2012 update: a report from the American Heart Association. *Circulation.* 2012; 125(1):e2-220.

Reference No. 2—C. Y. Wu, L. L. Chuang, K. C. Lin, H. C. Chen and P. K. Tsay, Randomized trial of distributed constraint-induced therapy versus bilateral arm training for the rehabilitation of upper-limb motor control and function after stroke. *Neurorehab Neural Re*, Vol. 25, 2, pp. 130-139, 2011.

Reference No. 3—J. H. Cauraugh, N. Lodha, S. K. Naik and J. J. Summers, Bilateral movement training and stroke motor recovery progress: a structured review and meta-analysis. *Hum Movement Sci*, Vol 29, 5, pp. 853-870, 2010.

Reference No. 4—C. Ausenda and M. Carnovali, Transfer of motor skill learning from the healthy hand to the paretic hand in stroke patients: a randomized controlled trial. *Eur J Phys Rehabil Med*, Vol. 47, 3, pp. 417-425, 2011.

Reference No. 5—G. Burdea, Virtual rehabilitation-benefits and challenges. *J Meth Inform Med*, pp. 519-523, 2003.

Reference No. 6—C. Brooks, B. Gabella, R. Hoffman, D. Sosin, and G. Whiteneck, Traumatic brain injury: designing and implementing a population-based follow-up system. *Arch Phys Med Rehab,* 78, pp. S26-S30, 1997.

Reference No. 7—M. Wang, N. J. Gamo, Y. Yang, L. E. Jin, X. J. Wang, et al., Neuronal basis of age-related working memory decline, *Nature*, Vol 476, pp. 210-213, July, 2011.

Reference No. 8—K. Lin, Y. Chen, C. Chen, C. Y. Wu and Y. F. Chang, The effects of bilateral arm training on motor control and functional performance in chronic stroke: a randomized controlled study, *Neurorehab Neural Re*, Vol 24; pp. 42-51, 2010.

Reference No. 9—P. W. Duncan, M. Probst, and S. G. Nelson, Reliability of the Fugl-Meyer assessment of sensorimotor recovery following cerebrovascular accident. *Phys Ther*, Vol 63, pp. 1606-1610, 1983.

Reference No. 10—G. Optale, C. Urgesi, V. Busato, S. Marin, L. Piron et al., Controlling memory impairment in elderly adults using virtual reality memory training: a randomized controlled pilot study. *Neurorehab Neural Re*, Vol 24, 4, pp. 348-357, 2010.

Reference No. 11—Unity Technologies, Reference Manual. San Francisco, Calif., 2010.

Reference No. 12—Sixense Entertainment, Razer Hydra Master Guide, 11 pp., 2011.

Reference No. 13—CNet Leap Motion controller review: Virtual reality for your hands. Jul. 22, 2013. http://reviews.cnet.com/input-devices/leap-motion-controller/4505-3133_7-35823002.html.

Reference No. 14—G. Burdea and M. Golomb, U.S. patent application Ser. No. 12/422,254 "Method for treating and exercising patients having limited range of body motion, Apr. 11 2009.

Reference No. 15—G. Burdea, D. Cioi, J. Martin, D. Fensterheim and M. Holenski,The Rutgers Arm II rehabilitation system—a feasibility study, *IEEE Trans Neural Sys Rehab Eng*, Vol 18, 5, pp. 505-514, 2010.

Reference No. 16—G. Burdea, C. Defais, K. Wong, J. Bartos and J. Hundal, "Feasibility study of a new game-based bimanual integrative therapy," Proceedings 10$^{th}$ Int. Conference on Virtual Rehabilitation, Philadelphia, Pa., August 2013, pp. 101-108.

Reference No. 17—G. Burdea, K. Polistico, A. Krishnamoorthy, J. Hundal, F. Damiani, S. Pollack, "A Feasibility study of BrightBrainer™ cognitive therapy for elderly nursing home residents with dementia," Disability and Rehabilitation—Assistive Technology.

Reference No. 18—Alzheimer's Association (2013) Alzheimer's Disease Facts and Figures. http://www.alz.org/downloads/factsfigures2013.pdf Reference No. 19—Budea G, (2013) Bi manual Integrative Virtual Rehabilitation Systems and Methods. US Patent Application US 2014/0121018 A1, Sep. 20, 2013.

Reference No. 20—Burdea G, C. Defais, K. Wong, et al. (2013). Feasibility study of a new game-based bimanual integrative therapy," Proceedings 10th Int. Conference on Virtual Rehabilitation, Philadelphia, Pa., August, pp. 101-108.

Reference No. 21—Burdea G, K Polistico, A Krishnamoorthy, G House, D Rethage, J Hundal, F qamiani, and S Pollack (2014) A feasibility study of the BrightBrainerlw cognitive therapy system for elderly nursing home residents with dementia," Disability and Rehabilitation—Assistive Technology, Vol. 9, 12 pp. Mar. 29 2014 early online.

Reference No. 22—Hardy J, D Drescher, K Sarkar et al. (2011). Enhancing visual attention and working memory with a Webbased cognitive training program. Mensa Research Journal. 42(2):13-20.

Reference No. 23—House G, G Burdea, K. Polistico, J. Ross, and M. Leibick. (2014) A serious-gaming alternative to pen-andpaper cognitive scoring—a pilot study. Int. Conference on Disability and Virtual Reality Technology, Sweden, 2014.

Reference No. 24—Rosenzweig A (2010) The Mini-Mental State Exam and Its Use as an Alzheimer's Screening Test. Online at http://alzheimers.about.com/od/testsandprocedures/a/The-Mini-Mental-State-Exam-And-Its-Use-As-An-Alzheinners-Screening-Test.htm Reference No. 25—Sixense Entertainment (2013) STEM system. Wireless motion tracking. http://sixense.com/hardware/wireless Reference No. 26—Alzheimer's Association, (2013), Alzheimer's Disease Facts and Figures. http://www.alz.org/downloads/facts_figures_2013.pdf Reference No. 27—Boulay, M, Benveniste, S, Boespflug, S et al., (2011), A pilot usability study of MINWii, a music therapy game for demented patients, Technol Health Care, 19, 4, pp. 233-246.

Reference No. 28—Burdea, G, Rabin, B, Rethage, D, et. al., (2013a), BrightArm™ Therapy for Patients with Advanced Dementia: A Feasibility Study, Proc. 10th Int. Conf. Virtual Rehab, Philadelphia, pp. 208-209.

Reference No. 29—Burdea, G, Defais, C, Wong, K, et al., (2013b), Feasibility study of a new game-based bimanual integrative therapy, Proc. 10th Int. Conf. Virtual Rehab, Philadelphia, pp. 101-108.

Reference No. 30—Burdea, G, Polistico, K, Krishnamoorthy, A, et al., (2014), A feasibility study of the BrightBrainer™ cognitive therapy system for elderly nursing home residents with dementia. Disability and Rehabilitation—Assistive Technology, 9, 12 pp. Mar. 29 2014 early online.

Reference No. 31—Folstein, M F, Folstein, S E, and Fanjiang, G., (2001), Mmse mini-mental state examination clinical guide. Lutz, F L: Psychological Assessment Resources, Inc.

Reference No. 32—Hebert, L E, Beckett, L A, Scherr, P A, et al. (2001), Annual incidence of Alzheimer disease in the United States projected to the years 2000 through 2050. Alzheimer Dis Assoc Disord. 15, 4, pp. 169-173.

Reference No. 33—Laerd Statistics, (2013), Spearman's Rank-Order Correlation using SPSS. Online at https://statistics.laerd.com/spss-tutorials/spearmans-rank-order-correlation-using-spss-statistics.php Reference No. 34—Lee, J H, Ku, J, Cho, W, et al., (2003), A virtual reality system for the assessment and rehabilitation of the activities of daily living, Cyberpsychol Behav, 6, 4, pp. 383-388.

Reference No. 35—McKhann, G., Knopman, D S, Howard Chertkow, H., et al., (2011), The diagnosis of dementia due to Alzheimer's disease: Recommendations from the National Institute on Aging—Alzheimer's Association workgroups on diagnostic guidelines for Alzheimer's disease. Alzheimer's & Dementia: Journal of Alzheimer's Association. 7, 3, pp. 263-269.

Reference No. 36—O'Bryant S, Lacritz L, Hall J et al. (2010). Validation of the new interpretive guidelines for the clinical dementia rating scale sum of boxes score in the national Alzheimer's coordinating center database. Arch Neurol, 67, 6, pp. 746-749.

Reference No. 37—Perneczky R, Wagenpfeil S, Komossa K, et al. (2006). Mapping scores onto stages: mini-mental state examination and clinical dementia rating. Am J Geriatr Psychiatry, 2, pp. 139-144.

Reference No. 38—Rabin, B, Burdea, G, Roll, D, et al., (2012), Integrative rehabilitation of elderly stroke survivors: The design and evaluation of the BrightArm. Disability and Rehabilitation—Assistive Technology. 7, 4, pp. 323-335.

Reference No. 39—Rosenzweig, A, (2010), The Mini-Mental State Exam and Its Use as an Alzheimer's Screening Test. Online at http://alzheimers.about.com/od/testsandprocedures/a/The-Mini-Mental-State-Exam-And-Its-Use-As-An-Alzheimers-Screening-Test.htm Reference No. 40—Rothbaum, B O, Hodges, L, Alarcon, R, et al., (1999), Virtual reality exposure therapy for PTSD Vietnam veterans: A case study, J Traumatic Stress, 12, 2, pp. 263-271.

Reference No. 41—Sixense Entertainment, (2011), Razer Hydra Master Guide, 11 pp. Unity Technologies, (2012), User Manual. San Francisco, Calif. http://docs.unity3d.com/Documentation/Manual/index.html While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims and in view of the specification.

The invention claimed is:

1. A system of screening a patient for cognitive impairment comprising:
   a computer;
   a videogame executing on the computer;
   a display portraying action from the videogame, the action being viewable by the patient;
   a game controller connected to the computer having one or more hand-held components with a button or trigger, wherein the hand-held components can be moved independently from one another;
   the game controller adapted to send to the computer one or more signals representative of a position of the hand-held component and a position of the button or trigger on the hand held component;
   the game controller adapted to send the one or more signals as the patient changes the position of the hand-held component and the position of the button or trigger on the hand held component in response to action from the videogame;
   the computer adapted to quantify a measure of cognitive impairment based on the one or more signals received by the controller and by compounding performance in one or more games,
   wherein the computer accounts for the uni-manual or bimanual interaction modality with the one or more video games and adjusts a testing score of cognitive impairment accordingly.

2. The system of claim 1, wherein the computer measures the amount of time it takes a patient to complete a task in the videogame and uses the time to generate a testing score of cognitive impairment.

3. The system of claim 1, wherein the computer measures the precision of movement of the controller during performance of a task on the videogame and uses that quantified precision of movement to generate a testing score of cognitive function.

4. The system of claim 1, wherein the computer measures the precision of movement of the controller during performance of a task in the video game and measures the time it takes a patient to complete the task in the video game and uses the quantified precision and quantified time to generate a testing score of cognitive impairment.

5. The system of claim 1, wherein the computer adjusts the measure of cognitive impairment based on the difficulty of the task performed in the video game.

6. The system of claim 1, wherein the computer quantifies cognitive impairment based on the patient's performance in two or more different types of games by computing an aggregate or compound score for the evaluation session.

7. The system of claim 1, wherein the computer quantifies cognitive impairment of the patient into one of the following cognitive bands: normal; mild cognitive impairment; moderate cognitive impairment; severe cognitive impairment.

8. The system of claim 1, wherein the game controller comprises two hand-held components with a button, wherein the hand-held components can be moved independently from one another in each hand of the patient.

9. A method of screening a patient for cognitive impairment comprising the steps of:
   executing a video game on a computer and portraying action from the videogame on a display, the action on the display being viewable by the patient;
   the patient holding a game controller connected to the computer, the game controller comprising one or more hand-held components having a button or trigger, wherein the one or more hand-held components can be moved independently from one another;
   the patient performing an action in the video game by moving the relative position of the one or more hand-held components and manipulating the button or trigger on the one or more hand-held components;
   the game controller sending and the computer receiving one or more signals from the game controller representative of the position of the one or more hand-held components and the position of the button or trigger on the one or more hand held components as the patient changes the position of the one or more hand held components and the position of the button or trigger on the hand held component in response to action from the videogame;
   the computer quantifying a measure of cognitive impairment based on the one or more signals received by the controller and by compounding performance in one or more games, the computer accounting for the uni-manual or bimanual interaction modality with the one or more video games and adjusting a testing score of cognitive impairment accordingly.

10. The method of claim 9, further comprising the computer measuring the amount of time it takes a patient to complete a task in the videogame and using that time to generate the testing score of cognitive impairment.

11. The method of claim 9, further comprising the computer measuring the precision of movement of the controller during performance of a task on the videogame and using that quantified precision of movement to generate the testing score of cognitive impairment.

12. The method of claim 9, further comprising the computer measuring the precision of movement of the controller during performance of a task in the video game and measuring the time it takes a patient to complete the task in the video game and using the quantified precision and quantified time to generate the testing score of cognitive impairment.

13. The method of claim 9, further comprising the computer adjusting the measure of cognitive impairment based on the difficulty of the task performed in the video game, and averaging performance scoring over a multitude of games played at different difficulty levels in a given evaluation session.

14. The method of claim 9, further comprising the computer quantifying cognitive impairment based on the patient's performance in two or more different types of games.

15. The method of claim 9, further comprising the computer quantifying cognitive impairment based on the patient's performance, said performance being measured after the patient had undergone a tutorial session such that learning artifacts are minimized.

16. The method of claim 9, further comprising the computer quantifying cognitive impairment of the patient into one of the following cognitive bands: normal; mild cognitive impairment; moderate cognitive impairment; severe cognitive impairment.

17. The method of claim 9, wherein the controller comprises two hand-held components with a button, wherein the hand-held components can be moved independently from one another in each hand of the patient.

* * * * *

UNITED STATES PATENT AND TRADEMARK OFFICE
CERTIFICATE OF CORRECTION

PATENT NO. : 10,694,990 B2  
APPLICATION NO. : 14/841042  
DATED : June 30, 2020  
INVENTOR(S) : Burdea et al.

Page 1 of 1

It is certified that error appears in the above-identified patent and that said Letters Patent is hereby corrected as shown below:

On the Title Page

Column 2, Line 1 under Reference Cited, the first listed U.S. Patent listed as 63,334,78 should be deleted and replaced with U.S. Patent No. 6,334,778

Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*